US008362309B2

(12) United States Patent
Julien et al.

(10) Patent No.: US 8,362,309 B2
(45) Date of Patent: Jan. 29, 2013

(54) FRAGRANCE AND METHODS FOR PRODUCTION OF 5-EPI-β-VETIVONE, 2-ISOPROPYL-6,10-DIMETHYL-SPIRO[4.5]DECA-2,6-DIEN-8-ONE, AND 2-ISOPROPYL-6,10-DIMETHYL-SPIRO[4.5]DECA-1,6-DIEN-8-ONE

(75) Inventors: Bryan N. Julien, Lexington, KY (US); David M. Wallace, San Diego, CA (US)

(73) Assignee: Allylix, Inc., San Diego, CA (US)

(*) Notice: Subject to any disclaimer, the term of this patent is extended or adjusted under 35 U.S.C. 154(b) by 0 days.

(21) Appl. No.: 13/385,059

(22) Filed: Jan. 30, 2012

(65) Prior Publication Data

US 2012/0129235 A1    May 24, 2012

Related U.S. Application Data

(60) Division of application No. 12/579,232, filed on Oct. 14, 2009, now Pat. No. 8,124,811, which is a continuation-in-part of application No. 12/052,464, filed on Mar. 20, 2008, now Pat. No. 7,622,614.

(60) Provisional application No. 60/919,284, filed on Mar. 20, 2007.

(51) Int. Cl.
*C07C 2/76* (2006.01)
*C12P 5/00* (2006.01)

(52) U.S. Cl. ..................... 585/360; 435/166
(58) Field of Classification Search .............. 585/360; 435/166
See application file for complete search history.

(56) References Cited

U.S. PATENT DOCUMENTS

| | | | |
|---|---|---|---|
| 3,962,147 A | 6/1976 | Maurer et al. | 252/522 |
| 4,261,866 A | 4/1981 | Barton et al. | 252/522 |
| 5,824,774 A | 10/1998 | Chappell et al. | 530/350 |
| 5,847,226 A | 12/1998 | Muller et al. | 568/346 |
| 6,072,045 A | 6/2000 | Chappell et al. | 536/23.1 |
| 6,468,772 B1 | 10/2002 | Chappell et al. | 435/183 |
| 6,495,354 B2 | 12/2002 | Chappell et al. | 435/183 |
| 6,531,303 B1 | 3/2003 | Millis et al. | 435/155 |
| 6,559,297 B2 | 5/2003 | Chappell et al. | 536/23.1 |
| 6,569,656 B2 | 5/2003 | Noel et al. | 435/183 |
| 6,645,762 B2 | 11/2003 | Chappell et al. | 435/325 |
| 6,689,593 B2 | 2/2004 | Millis et al. | 435/155 |
| 6,890,752 B2 | 5/2005 | Chappell et al. | 435/325 |
| 6,982,304 B2 | 1/2006 | Mure et al. | 526/106 |
| 7,186,891 B1 | 3/2007 | Chappell et al. | 800/298 |
| 7,405,057 B2 | 7/2008 | Chappell et al. | 435/69.1 |
| 7,442,785 B2 | 10/2008 | Chappell et al. | 536/23.6 |
| 7,622,614 B2 | 11/2009 | Julien et al. | 568/327 |
| 8,106,260 B2 | 1/2012 | Chappell et al. | 800/298 |
| 8,124,811 B2 | 2/2012 | Julien et al. | 568/367 |
| 8,192,950 B2 | 6/2012 | Chappell et al. | 435/41 |
| 2002/0111517 A1 | 8/2002 | Ahlers et al. | 568/451 |
| 2003/0166255 A1 | 9/2003 | Chappell | 435/252.3 |
| 2004/0078840 A1 | 4/2004 | Chappell et al. | 800/278 |
| 2004/0249229 A1 | 12/2004 | Gee et al. | 585/664 |
| 2006/0052240 A1 | 3/2006 | Sakai | 502/202 |
| 2006/0194960 A1 | 8/2006 | Kim et al. | 540/1 |
| 2006/0218661 A1 | 9/2006 | Chappell et al. | 800/278 |
| 2006/0222671 A1 | 10/2006 | Weidner | 424/401 |
| 2006/0293549 A1 | 12/2006 | Sigl et al. | 585/670 |
| 2007/0089198 A1 | 4/2007 | Chappell et al. | 800/280 |
| 2007/0231861 A1 | 10/2007 | Millis et al. | 435/69.1 |
| 2007/0238157 A1 | 10/2007 | Millis et al. | 435/166 |
| 2007/0238159 A1 | 10/2007 | Millis et al. | 435/252.33 |
| 2007/0238160 A1 | 10/2007 | Millis et al. | 435/252.33 |
| 2007/0254354 A1 | 11/2007 | Millis et al. | 435/252.33 |
| 2008/0178354 A1 | 7/2008 | Chappell et al. | 800/298 |
| 2008/0233622 A1 | 9/2008 | Julien et al. | 435/148 |
| 2010/0035329 A1 | 2/2010 | Millis et al. | 435/254.2 |
| 2010/0120110 A1 | 5/2010 | Chappell | 435/166 |
| 2010/0129306 A1 | 5/2010 | Julien et al. | 424/65 |
| 2010/0151519 A1 | 6/2010 | Julien et al. | 435/69.1 |
| 2010/0151555 A1 | 6/2010 | Julien et al. | 435/193 |
| 2010/0216186 A1 | 8/2010 | Chappell et al. | 435/69.1 |

FOREIGN PATENT DOCUMENTS

| | | |
|---|---|---|
| WO | WO 97/38703 | 10/1997 |
| WO | WO 00/17327 | 3/2000 |
| WO | WO 2006/014837 | 2/2006 |
| WO | WO 2006/079020 | 7/2006 |
| WO | WO 2006/134523 | 12/2006 |
| WO | WO 2008/116056 | 9/2008 |
| WO | WO 2010/019696 | 2/2010 |
| WO | WO 2012/058636 | 5/2012 |

OTHER PUBLICATIONS

Takahashi et al. Metabolic Engineering of Sesquiterpene Metabolism in Yeast. Biotechnology and Bioengineering, vol. 97, No. 1, May 1, 2007. 170-181.*

Takahashi et al. Functional Characterization of Premnaspirodiene Oxygenase, a Cytochrome P450 Catalyzing Regio- and Stereo-specific Hydroxylations of Diverse Sesquiterpene Substrates. Journal of Biological Chemistry, vol. 282, No. 43, Oct. 26, 2007. 31744-31754.*

Schenk et al. Stereochemistry and deuterium isotope effects associated with the cyclization-rearrangements catalyzed by tobacco epiaristolochene and *Hyoscyamus premnaspirodiene* synthases, and chimeric CH4 hybrid cyclase. Archives of Biochemistry and Biophysics, 2006, vol. 448, 31-44.*

Back et al. Cloning and Bacterial Expression of a Sesquiterpene Cyclase from *Hyoscyanumus muticus* and Its Molecular Comparison to Related Terpene Cyclases. Journal of Biological Chemistry, vol. 270, No. 13, Mar. 31, 1995, 7375-7381.*

(Continued)

*Primary Examiner* — Sikarl Witherspoon

(74) *Attorney, Agent, or Firm* — McKenna Long & Aldridge LLP; Stephanie Seidman

(57) ABSTRACT

The present invention is directed to novel methods for production of 5-epi-β-vetivone, 2-isopropyl-6,10-dimethyl-spiro[4.5]deca-2,6-dien-8-one and 2-isopropyl-6,10-dimethylspiro[4.5]deca-1,6-dien-8-one, which are useful for their fragrant qualities. Provided are methods for production of premnaspirodiene from a terpene substrate, methods for production of 5-epi-β-vetivone from premnaspirodiene as starting material, and methods for production of 2-isopropyl-6,10-dimethyl-spiro[4.5]deca-2,6-dien-8-one and 2-isopropyl-6,10-dimethyl-spiro[4.5]deca-1,6-dien-8-one from premnaspirodiene as starting material.

17 Claims, 6 Drawing Sheets

OTHER PUBLICATIONS

Dolan, K., "Allylix sniffs out biotech for new fragrances," found in Forbes Magazine dated Nov. 8, 2010, Published on Oct. 21, 2010 [online][retrieved on Jun. 1, 2012] Retrieved from: <URL:forbes.com/forbes/2010/1108/technology-allylix-fragrances-flavor-carolyn-fritz-smell-test.html?partner=email [1 page].

Quigley, K., "Allylix raises $18.2M, announces launch of new product for fragrance market," San Diego Business Journal, Published on Mar. 14, 2012 [online][retrieved on Jun. 1, 2012] Retrieved from:<URL:sdbj.com/news/2012/mar/14/allylix-raises-182m-announces-launch-new-product-f/ [1 page].

Response to Examination Report, submitted Mar. 20, 2012, in connection with corresponding Australian Patent Application No. 2009225306, 32 pages.

Notice of Acceptance, issued Mar. 30, 2012, in connection with corresponding Australian Patent Application No. 2009225306, 3 pages.

Response to European Search Report, submitted Jul. 31, 2012, in connection with corresponding European Patent Application No. 08732550.2, 16 pages.

Arantes et al., "The preparation and microbiological hydroxylation of the sesquiterpenoid nootkatone," J. Chem. Res. (Synopsis) 3:248 (1999).

Back, K. and J. Chappell, "Cloning and bacterial expression of a sesquiterpene cyclase from *Hyoscyamus muticus* and its molecular comparison to related terpene cyclases," J. Biol. Chem. 270:7375-7381 (1995).

Back, K. and J. Chappell, "Identifying functional domains within terpene cyclases using a domain-swapping strategy," Proc. Natl. Acad. Sci. U.S.A. 93:6841-6845 (1996).

Blay et al., "Synthesis of spirovetivane sesquiterpenes from santonin. Synthesis of (+)-anhydro-β-rotunol and all diasteromers of 6,11-spirovetivadiene," J. Org. Chem. 69:7294-7302 (2004).

Brake, A., "α-Factor leader-directed secretion of heterologous proteins from yeast," Meth. Enzymol. 185:408-421 (1991).

Burns, N., "The vetivane sesquiterpenes," The Baran Laboratory at Scripps Research Institute Group Meeting (Dec. 15, 2004).

Butterworth et al., "Environmentally friendly catalysis using supported reagents: catalytic epoxidation using a chemically modified silica gel," Chem. Comm. 16:1859-1860 (1996).

Caine et al., "Acid-catalyzed rearrangements of cyclopropyl ketones related to eudesmane," J. Org. Chem. 45:3798-3802 (1980).

Chappell, J., "Valencene synthase—a biochemical magician and harbinger of transgenic aromas," Trends Plant Sci. 9(6):266-269 (2004).

Chisem et al., "Liquid phase oxidations using novel surface functionalised silica supported metal catalysts," Chem. Comm. 22:2203-2204 (1997).

Chisholm et al., "Molecular and genetic approach to enhancing protein secretion," Meth. Enzymol. 185:471-482 (1991).

Collins et al., "Aldehydes from primary alcohols by oxidation with chromium trioxide: heptanal," Org. Synth. Coll. vol. 6:644 (1988); vol. 52:5 (1972).

Deshpande, M., "Ethanol production from cellulose by coupled saccharification/fermentation using *Saccharomyces cerevisiae* and cellulase complex from *Sclerotiun rolfsii* UV-8 mutant," Appl. Biochem. Biotechnol. 36:227-234 (1992).

Donahue, T. and Cigan, A., "Sequence and structural requirements for efficient translation in yeast," Meth. Enzymol. 185:366-372 (1991).

Eilerman et al., "A new spiro-annelation procedure: intramolecular decarboxylative alkylation of β-keto-esters," J.Chem.Soc. Chem. Comm. 1:30-32 (1981).

Emr, S., "Heterologous gene expression in yeast," Meth. Enzymol. 185:231-233 (1991).

Endo et al., "α-Vetivone," Chem. Pharm. Bull. 17(7):1324-1331 (1969).

Etcheverry et al., "Induced expression using yeast copper metallothionein promoter," Meth. Enzymol. 185:319-329 (1991).

Frykman et al., "Characterization of product capture resin during microbial cultivations," J. Ind. Microbiol. Biotechnol. 33:445-453 (2006).

Greenhagen et al., "Identifying and manipulating structural determinates linking catalytic specificities in terpene synthases," Proc. Natl. Acad. Sci. U.S.A. 103:9826-9831 (2006).

Hitzeman et al., "Use of heterologous and homologous signal sequences for secretion of heterologous proteins from yeast," Meth. Enzymol. 185:421-440 (1991).

Hunter et al., "Conversion of valencene to nootkatone," J. Food Sci. 30(5):876-878 (1965).

Hutchins et al., "An efficient approach to spiro-sesquiterpenes. Synthesis of (±)β-vetivone," Synth. Comm. 14(5):445-451 (1984).

Hwu et al., "Silicon-promoted ring contraction in the formation of carbocyclic spiro compounds. Total synthesis of (-)-solavetivone," J. Org. Chem. 57:922-928 (1992).

Ishiwatari et al., "Application of pyrolysis-gas chromatography to the study of thermal alteration of chlorophyll-a: effect of clay minerals," J. Anal. App. Pyrol. 32:153-160 (1995).

Jones, E., "Vacuolar proteases in yeast *Saccharomyces cerevisiae*," Meth. Enzymol. 185:372-386 (1991).

Julien et al., "Heterologous expression of the epothilone biosynthetic genes in *Myxococcus xanthus*," Antimicrob. Agents Chemother. 46:2772-2778 (2002).

Kendall et al., "Cotranslation amino-terminal processing," Meth. Enzymol. 185:398-407 (1991).

Kingsman et al., "High efficiency yeast expression vectors based on the promoter of the phosphoglycerate kinase gene," Meth. Enzymol. 185:329-341 (1991).

Kjonaas et al., "Acid catalyzed isomerization of carvone to carvacrol," J. Chem. Educ. 82(12):1813-1814 (2005).

Lindahl et al., "Production of artemisinin precursor amorpha-1,4-diene by engineered *Saccharomyces cerevisiae*," Biotechnol. Lett. 28:571-580 (2006).

Murai et al., "π-Cyclization: the synthesis of (±)-solavetivone and (±)-hinesol," Tetrahedron Lett. 22:1033-1036 (1981).

Mylin et al., "Regulated *GAL4* expression cassette providing controllable and high level optput from high copy galactose promoters in yeast," Meth. Enzymol. 185:297-308 (1991).

Nakazaki et al., "Stereoselective total synthesis of (±)-α-vetispirene, (±)-hinesol, and (±)-β-vetivone based on a Claisen rearrangement," Tetrahedron 62:6264-6271 (2006).

Park et al., "Metabolic engineering of *Saccharomyces cerevisiae* for the fermentative production of high-value terpenoid compounds," Abstract of presentation at Society for Industrial Microbiology Annual Meeting and Exhibition, Denver, CO (Jul. 30, 2007).

Park et al., "Using *Saccharomyces cerevisiae* for production of terpenoid compounds for use as fragrances and flavorings," Abstract of presentation at Society for Industrial Microbiology Annual Meeting and Exhibition, San Diego, CA (Aug. 13, 2008).

Price et al., "Expression of heterologous proteins in *Saccharomyces cerevisiae* using the ADH2 promoter," Meth. Enzymol. 185:308-318 (1991).

Rose, A. and J. Broach, "Propagation and expression of cloned genes in yeast: 2-μm circle-based vectors," Meth. Enzymol. 185:234-279 (1991).

Rosenberg et al., "Glyceraldehyde-3-phosphate dehydrogenase-derived expression cassettes for constitutive synthesis of heterologous proteins," Meth. Enzymol. 185:341-350 (1991).

Salvador et al., "Copper-catalysed allylic oxidation of $\Delta^5$-steroids by t-butyl hydroperoxide," Tetrahedron Lett. 38(1):119-122 (1997).

Salvador et al., "The allylic oxidation of unsaturated steroids by tert-butyl hydroperoxide using surface functionalised silica supported metal catalysts," Green Chem. 4:352-356 (2002).

Saunders et al., "The use of a hydrophobic resin as a product reservoir in steroid transformations," Biotechnol. Bioeng. 27(6):825-831 (1985).

Schenk et al., "Stereochemistry and deuterium isotope effects associated with the cyclization—rearrangements catalyzed by tobacco epiaristolochene and *Hyoscyamus premnaspirodiene* synthases, and the chimeric CH4 hybrid cyclase," Arch. Biochem. Biophys. 448:31-44 (2006).

Sharma et al., "Allylic oxidation in terpenoids: synthesis of (±)-E-linalool-1-oic acid, (+)-E-9-hydroxylinalool and (+)-7-hydroxyterpineol," Proc. Indian. Acad. Sci. (Chem. Sci.) 108(1):21-26 (1996).

Sharon-Asa et al., "Citrus fruit flavor and aroma biosynthesis: isolation, functional characterization, and developmental regulation of Cstps 1, a key gene in the production of the sesquiterpene aroma compound valencene," Plant J. 36:664-674 (2003).

Silvestre et al., "Allylic and benzylic oxidation reactions with sodium chlorite," Tetrahedron 63:2439-2445 (2007).

Sledziewski et al., "Superimposition of temperature regulation on yeast promoters," Meth. Enzymol. 185:351-366 (1991).

Sowden et al., "Biotransfomation of the sesquiterpene (+)-valencene by cytochrome P450cam and P450BM-3," Org. Biomol. Chem. 3:57-64 (2005).

Stearns et al., "Manipulating yeast genome using plasmid vectors," Meth. Enzymol. 185:280-297 (1991).

Takahashi et al., "Functional characterization of premnaspirodiene oxygenase, a cytochrome P450 catalyzing regio- and stereo-specific hydroxylations of diverse sesquiterpene substrates," J. Biol. Chem. 43:31744-31754 (2007).

Takahashi et al., "Metabolic engineering of sesquiterpene metabolism in yeast," Biotechnol. Bioeng. 97:170-181 (2007).

Takemoto et al., "Diasteroselective total synthesis of (–)-solavetivone via a copper-catalzyed conjugate addition of $Me_3Al$ to a cyclohexa-2,5-dienone intermediate," Tetrahedron 53(2):603-616 (1997).

van Der Gen et al., "Stereoselective synthesis of eremophilane sesquiterpenoids from β-pinene," Recueil des Travaux Chimiques des Pays-Bas 90(9):1034-1044 (1971).

Wilkinson, "Detection and inhibition of ubiquitin-dependent proteolysis," Meth. Enzymol. 185:387-397 (1991).

Wilson et al., "Synthesis of nootkatone from valencene," J. Agric. Food Chem. 26(6):1430-1432 (1978).

Woo et al., "Migrastatin and a new compound, isomigrastatin, from Streptomyces platensis," J. Antibiot. 55:141-146 (2002).

International Search Report and Written Opinion, issued Oct. 7, 2008, in connection with corresponding International Patent Application No. PCT/US08/57639, 12 pages.

International Preliminary Report on Patentability, issued Mar. 18, 2009, in connection with corresponding International Patent Application No. PCT/US08/57639, 6 pages.

Notice of Allowance, issued Jul. 14, 2009, in connection with corresponding U.S. Appl. No. 12/052,464, 10 pages.

Office Action, issued May 9, 2011, in connection with corresponding U.S. Appl. No. 12/579,232, 6 pages.

Examination Report, issued Sep. 28, 2011, in connection with corresponding Australian Patent Application No. 2009225306, 3 pages.

Notice of Allowance, issued Oct. 19, 2011, in connection with corresponding U.S. Appl. No. 12/579,232, 8 pages.

Extended European Search Report, issued Jan. 4, 2012, in connection with corresponding European Patent Application No. 08732550.2, 12 pages.

Allylix, "Protein engineering and chembiosynthesis to produce novel sesquiterpenoids," Presentation at BIO World Congress on Industrial Biotechnology & Bioprocessing, Washington, D.C. (Jun. 28, 2010). [19 pages].

* cited by examiner 5-epi-β-vetivone (1)

(-)-Premnaspirodiene (2)

2-isopropyl-6,10-dimethyl-spiro[4.5]deca-2,6-dien-8-one (3)

2-isopropyl-6,10-dimethyl-spiro[4.5]deca-1,6-dien-8-one (4)

FRAGRANCE AND METHODS FOR PRODUCTION OF 5-EPI-β-VETIVONE, 2-ISOPROPYL-6,10-DIMETHYL-SPIRO[4.5]DECA-2,6-DIEN-8-ONE, AND 2-ISOPROPYL-6,10-DIMETHYL-SPIRO[4.5]DECA-1,6-DIEN-8-ONE

RELATED APPLICATIONS

This application is a divisional of allowed U.S. patent application Ser. No. 12/579,232, filed Oct. 14, 2009, now U.S. Pat. No. 8,124,811 which is a continuation-in-part of U.S. patent application Ser. No. 12/052,464, filed Mar. 20, 2008, now U.S. Pat. No. 7,622,614 which claims priority to U.S. Provisional Application Ser. No. 60/919,284, filed Mar. 20, 2007. The subject matter of each of these applications is incorporated herein by reference in its entirety.

FIELD OF THE INVENTION

The present invention is directed to novel methods for production of 5-epi-β-vetivone, 2-isopropyl-6,10-dimethyl-spiro[4.5]deca-2,6-dien-8-one and 2-isopropyl-6,10-dimethyl-spiro[4.5]deca-1,6-dien-8-one, which are useful for their fragrant qualities. In one embodiment the present invention describes a method for production of 5-epi-β-vetivone by the use of premnaspirodiene as starting material. In another embodiment, the present invention describes a method for production of 2-isopropyl-6,10-dimethyl-spiro[4.5]deca-2,6-dien-8-one and 2-isopropyl-6,10-dimethyl-spiro[4.5]deca-1,6-dien-8-one by the use of premnaspirodiene as starting material. In yet another embodiment, the present invention describes a novel method for production of premnaspirodiene from a terpene substrate. Use of the fragrant components or any composition containing the component can be advantageously employed in the perfumery, personal care and consumer products industries.

BACKGROUND OF THE INVENTION

The present invention relates to the field of fragrance compounds and compositions. In particular, the invention concerns the method of production of fragrance compositions as well as their use as, e.g., perfuming, personal care and consumer product ingredients.

5-epi-β-vetivone, represented by Formula (1) below:

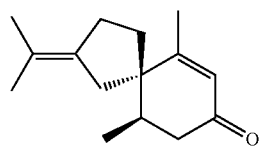

Formula (1)

is a potentially valuable fragrance component or perfuming ingredient due to its vetivert, woody, grapefruit aroma. Similarly, the mixture of 2-isopropyl-6,10-dimethyl-spiro[4.5]deca-2,6-dien-8-one, represented by Formula (3) below

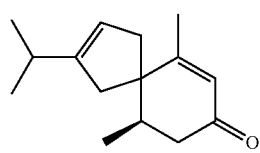

Formula (3)

and 2-isopropyl-6,10-dimethyl-spiro[4.5]deca-1,6-dien-8-one, represented by Formula (4) below

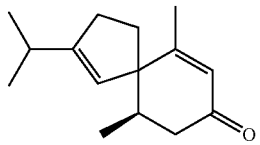

Formula (4)

is a potentially valuable fragrance component as well, due to its vetivert, woody, grapefruit aroma.

One method of producing 5-epi-β-vetivone has been developed to date (11). In this process 5-epi-β-vetivone was made as a byproduct during the diastereoselective 1,4-addition of a methyl group to a double bond to synthesize (−)-solavetivone (5). However, 5-epi-β-vetivone is made as a byproduct and the disclosed process is not suitable for commercial grade production of 5-epi-β-vetivone.

No methods of producing 2-isopropyl-6,10-dimethyl-spiro[4.5]deca-2,6-dien-8-one (3) and 2-isopropyl-6,10-dimethyl-spiro[4.5]deca-1,6-dien-8-one (4) are known to date.

Therefore, there is a current need in the art for methods to produce 5-epi-β-vetivone (1) in a fewer number of reaction steps, with higher overall yield, and from less expensive and more available starting materials. Furthermore, there is a current need in the art for methods to produce 2-isopropyl-6,10-dimethyl-spiro[4.5]deca-2,6-dien-8-one (3) and 2-isopropyl-6,10-dimethyl-spiro[4.5]deca-1,6-dien-8-one (4).

Accordingly, the present invention is directed to novel methods for production of 5-epi-β-vetivone, 2-isopropyl-6,10-dimethyl-spiro[4.5]deca-2,6-dien-8-one (3) and 2-isopropyl-6,10-dimethyl-spiro[4.5]deca-1,6-dien-8-one (4), which are useful for their fragrant qualities. The production of the fragrance compositions as described by the present invention can be used for the preparation of perfumes, household products, laundry products, body care products or cosmetic products, as well as related compositions and articles. Mixtures of the compound described in the invention, a fragrance modifying composition, a perfume composition and a cologne composition are also included in the invention. The compounds and compositions can be employed in order to confer a woody, grapefruit, or vetivert odor to a variety of products.

SUMMARY OF THE INVENTION

In one embodiment the present invention describes a method for synthesizing 5-epi-β-vetivone (1) comprising the steps of:
(1) subjecting (−)-premnaspirodiene (2) to oxidation of an allylic carbon to form (−)-solavetivone; and
(2) subjecting the (−)-solavetivone (5) formed in step (1) to acid-catalyzed isomerization to form 5-epi-β-vetivone (1);
wherein time and temperature conditions for step (2) are such that the predominant product is 5-epi-β-vetivone (1).

In another embodiment the present invention describes a method for synthesizing a mixture of 2-isopropyl-6,10-dimethyl-spiro[4.5]deca-2,6-dien-8-one (3) and 2-isopropyl-6,10-dimethyl-spiro[4.5]deca-1,6-dien-8-one (4) comprising the steps of:
(1) subjecting (−)-premnaspirodiene (2) to oxidation of an allylic carbon to form (−)-solavetivone (5); and
(2) subjecting the (−)-solavetivone (5) formed in step (1) to acid-catalyzed isomerization to form the mixture of 2-isopropyl-6,10-dimethyl-spiro[4.5]deca-2,6-dien-8-one (3) and 2-isopropyl-6,10-dimethyl-spiro[4.5]deca-1,6-dien-8-one (4);

wherein time and temperature conditions for step (2) are such that the predominant product is a mixture of 2-isopropyl-6,10-dimethyl-spiro[4.5]deca-2,6-dien-8-one (3) and 2-isopropyl-6,10-dimethyl-spiro[4.5]deca-1,6-dien-8-one (4).

In another embodiment the present invention describes a substantially purified and isolated mixture of 2-isopropyl-6,10-dimethyl-spiro[4.5]deca-2,6-dien-8-one (3) and 2-isopropyl-6,10-dimethyl-spiro[4.5]deca-1,6-dien-8-one (4).

In another embodiment the present invention describes the substantially purified and isolated compound 2-isopropyl-6,10-dimethyl-spiro[4.5]deca-2,6-dien-8-one (3), substantially free of 2-isopropyl-6,10-dimethyl-spiro[4.5]deca-1,6-dien-8-one (4).

In another embodiment the present invention describes the substantially purified and isolated compound 2-isopropyl-6,10-dimethyl-spiro[4.5]deca-1,6-dien-8-one (3), substantially free of 2-isopropyl-6,10-dimethyl-spiro[4.5]deca-2,6-dien-8-one (4).

In another embodiment the present invention describes a method for producing (−)-premnaspirodiene (2) from a terpene substrate, comprising the steps of:
(1) providing the terpene substrate to a host cell transformed or transfected with a vector comprising a sequence encoding a *Hyoscyamus muticus* premnaspirodiene synthase gene;
(2) culturing the host cell under conditions suitable to produce (−)-premnaspirodiene (2) from the terpene substrate; and
(3) isolating the (−)-premnaspirodiene (2).

In another embodiment the present invention describes a method for synthesizing 5-epi-β-vetivone comprising the steps of:
(1) providing a terpene substrate to a host cell transformed or transfected with a vector comprising a sequence encoding a *Hyoscyamus muticus* premnaspirodiene synthase gene;
(2) culturing the host cell under conditions suitable to produce (−)-premnaspirodiene from the terpene substrate; and
(3) isolating the (−)-premnaspirodiene;
(4) subjecting the isolated (−)-premnaspirodiene to oxidation of an allylic carbon to form (−)-solavetivone; and
(5) subjecting the (−)-solavetivone formed in step (4) to acid-catalyzed isomerization to form 5-epi-β-vetivone;
wherein time and temperature conditions for step (5) are such that the predominant product is 5-epi-β-vetivone.

In another embodiment the present invention describes a method for synthesizing a mixture of 2-isopropyl-6,10-dimethyl-spiro[4.5]deca-2,6-dien-8-one and 2-isopropyl-6,10-dimethyl-spiro[4.5]deca-1,6-dien-8-one comprising the steps of:
(1) providing a terpene substrate to a host cell transformed or transfected with a vector comprising a sequence encoding a *Hyoscyamus muticus* premnaspirodiene synthase gene;
(2) culturing the host cell under conditions suitable to produce (−)-premnaspirodiene from the terpene substrate; and
(3) isolating the (−)-premnaspirodiene;
(4) subjecting the isolated (−)-premnaspirodiene to oxidation of an allylic carbon to form (−)-solavetivone; and
(5) subjecting the (−)-solavetivone formed in step (4) to acid-catalyzed isomerization to form the mixture of 2-isopropyl-6,10-dimethyl-spiro[4.5]deca-2,6-dien-8-one and 2-isopropyl-6,10-dimethyl-spiro[4.5]deca-1,6-dien-8-one;
wherein time and temperature conditions for step (5) are such that the predominant product is the mixture of 2-isopropyl-6,10-dimethyl-spiro[4.5]deca-2,6-dien-8-one and 2-isopropyl-6,10-dimethyl-spiro[4.5]deca-1,6-dien-8-one.

In yet another embodiment the present invention describes a method for synthesizing 2-isopropyl-6,10-dimethyl-spiro[4.5]deca-2,6-dien-8-one comprising the steps of:
(1) providing a terpene substrate to a host cell transformed or transfected with a vector comprising a sequence encoding a *Hyoscyamus muticus* premnaspirodiene synthase gene;
(2) culturing the host cell under conditions suitable to produce (−)-premnaspirodiene from the terpene substrate; and
(3) isolating the (−)-premnaspirodiene;
(4) subjecting the isolated (−)-premnaspirodiene to oxidation of an allylic carbon to form (−)-solavetivone; and
(5) subjecting the (−)-solavetivone formed in step (4) to acid-catalyzed isomerization to form a mixture of 2-isopropyl-6,10-dimethyl-spiro[4.5]deca-2,6-dien-8-one and 2-isopropyl-6,10-dimethyl-spiro[4.5]deca-1,6-dien-8-one;
wherein time and temperature conditions for step (5) are such that the predominant product is the mixture of 2-isopropyl-6,10-dimethyl-spiro[4.5]deca-2,6-dien-8-one and 2-isopropyl-6,10-dimethyl-spiro[4.5]deca-1,6-dien-8-one; and
(6) isolating the 2-isopropyl-6,10-dimethyl-spiro[4.5]deca-2,6-dien-8-one from the mixture of 2-isopropyl-6,10-dimethyl-spiro[4.5]deca-2,6-dien-8-one and 2-isopropyl-6,10-dimethyl-spiro[4.5]deca-1,6-dien-8-one formed in step (5) by a method selected from the group consisting of thin-layer chromatography, column chromatography, gas chromatography, and countercurrent distribution.

In yet another embodiment the present invention describes a method for synthesizing 2-isopropyl-6,10-dimethyl-spiro[4.5]deca-1,6-dien-8-one comprising the steps of:
(1) providing a terpene substrate to a host cell transformed or transfected with a vector comprising a sequence encoding a *Hyoscyamus muticus* premnaspirodiene synthase gene;
(2) culturing the host cell under conditions suitable to produce (−)-premnaspirodiene from the terpene substrate; and
(3) isolating the (−)-premnaspirodiene;
(4) subjecting the isolated (−)-premnaspirodiene to oxidation of an allylic carbon to form (−)-solavetivone; and
(5) subjecting the (−)-solavetivone formed in step (4) to acid-catalyzed isomerization to form a mixture of 2-isopropyl-6,10-dimethyl-spiro[4.5]deca-2,6-dien-8-one and 2-isopropyl-6,10-dimethyl-spiro[4.5]deca-1,6-dien-8-one;
wherein time and temperature conditions for step (5) are such that the predominant product is the mixture of 2-isopropyl-6,10-dimethyl-spiro[4.5]deca-2,6-dien-8-one and 2-isopropyl-6,10-dimethyl-spiro[4.5]deca-1,6-dien-8-one; and
(6) isolating the 2-isopropyl-6,10-dimethyl-spiro[4.5]deca-1,6-dien-8-one from the mixture of 2-isopropyl-6,10-dimethyl-spiro[4.5]deca-2,6-dien-8-one and 2-isopropyl-6,10-dimethyl-spiro[4.5]deca-1,6-dien-8-one formed in step (e) by a method selected from the group consisting of thin-layer chromatography, column chromatography, gas chromatography, and countercurrent distribution. The present invention also includes a fragrance composition with a compound having the structure:

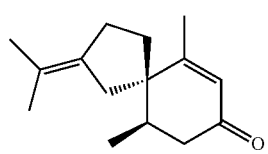

Formula (1)

in an amount effective to impart a fragrance. In one aspect, the compound of the fragrance composition is present in an amount of at least 0.01% by weight. In another aspect, the fragrance composition comprises an amount of the compound of Formula (1) effective to impart fragrance in combination with conventional fragrance ingredients.

Another object of the present invention is a perfumed product comprising a compound having the structure of Formula (1). The perfumed product can be a household product, such as, for example, a solid or liquid detergent, a fabric softener, an air freshener, a fabric refresher, an ironing water, a paper, a wipe or a bleach. The perfumed product can be a cosmetic product or a body care product, for example a perfume, a cologne or after-shave lotion, a perfumed soap, a shower or bath salt, mousse, oil or gel, a hygiene product, a hair care product, a shampoo, a deodorant or antiperspirant.

The present invention can be a perfuming composition containing the compound of Formula (1) in an amount sufficient to give a fragrance to the composition. In one embodiment, the perfuming composition can additionally contain at least one perfumery adjuvant.

Another aspect of the present invention is a fragrance application comprising a compound of Formula (1). The fragrance application can be, for example, a household product such as laundry product, a solid or liquid detergent, a fabric softener, an air freshener, a fabric refresher, an ironing water, a paper, a wipe or a bleach. In another aspect, the fragrance application can be a cosmetic product or body care product such as a perfume, a cologne or after-shave lotion, a perfumed soap, a shower or bath salt, mousse, oil or gel, a hygiene product, a hair care product, a shampoo, a deodorant or antiperspirant. A consumer product is a product which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one compound.

The invention also includes methods of imparting a woody, vetivert or grapefruit odor to a fragrance or fragrance composition by providing the compound of Formula (1) to the fragrance.

Methods of the invention include imparting, improving, enhancing or modifying a fragrance formulation through the addition of an olfactory acceptable amount of Formula (1). The olfactory acceptable amount can be from about 0.005 to about 10 weight percent of the fragrance formulation. In one aspect, the olfactory acceptable amount is from about 0.5 to about 8 weight percent of the fragrance formulation. In another aspect, the method of claim 18, wherein the olfactory acceptable amount is from about 1 to about 7 weight percent of the fragrance formulation.

The invention also includes a mixture comprising the compound of Formula (1) and an auxiliary ingredient compatible with the compound of Formula (1), the weight ratio of the compound of Formula (1) being in the range of from about 1:1 up to about 1:5.

The invention also includes a fragrance modifying composition comprising the compound of Formula (1) and an auxiliary ingredient compatible with the compound of Formula (1), the weight ratio of the compound of Formula (1) being in the range of from about 1:1 up to about 1:5.

Also included in the invention is a perfume composition comprising the compound of Formula (1) and at least one compatible adjuvant, the ratio of the compound of Formula (1) being in the range of from about 1:1 up to about 1:5.

The invention also includes a cologne composition comprising the compound of Formula (1) and at least one compatible adjuvant, the ratio of the compound of Formula (1) being in the range of from about 1:1 up to about 1:5. The invention also includes a method of using the compound of Formula (1) as a perfume. In one embodiment, the method of using the compound of Formula (1) as a perfume further comprises an auxiliary ingredient compatible with the compound of Formula (1).

Other features and advantages of the invention will become apparent from the following description of the preferred embodiments thereof and from the claims.

BRIEF DESCRIPTION OF THE DRAWINGS

The following invention will become better understood with reference to the specification, appended claims, and accompanying drawings, where:

FIG. 3 depicts the structural formulas of 2-isopropyl-6,10-dimethyl-spiro[4.5]deca-2,6-dien-8-one (3) (the "2,6-diene isomer") and 2-isopropyl-6,10-dimethyl-spiro[4.5]deca-1,6-dien-8-one (4) (the "1,6-diene isomer").

FIG. 7A shows the graph on a normal scale. FIG. 7B expands the scale to depict the impurities present in the premnaspirodiene before distillation.

FIG. 8A shows the graph on a normal scale. FIG. 8B expands the scale to depict the lack of impurities present in the premnaspirodiene after distillation.

DETAILED DESCRIPTION OF THE INVENTION 5-epi-β-vetivone (1) is commercially useful in the fragrance industry due to its vetivert, woody, grapefruit aroma. The present invention generally describes a method for production of 2-isopropylidene-6,10-dimethyl-spiro[4.5]dec-6-en-8-one (the "5-epi-β-vetivone"), represented by Formula (1), from (−) premnaspirodiene, represented by Formula (2) below:

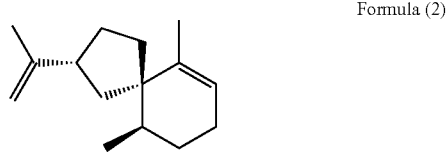

Formula (2)

In general, one embodiment of the present invention is a method for synthesizing 5-epi-β-vetivone comprising the steps of:

(1) subjecting (−)-premnaspirodiene (2) to oxidation of an allylic carbon to form (−)-solavetivone; and (2) subjecting the (−)-solavetivone (5) formed in step (i) to acid-catalyzed isomerization to form 5-epi-β-vetivone (1); wherein time and temperature conditions for step (ii) are such that the predominant product is 5-epi-β-vetivone.

Figure 5:
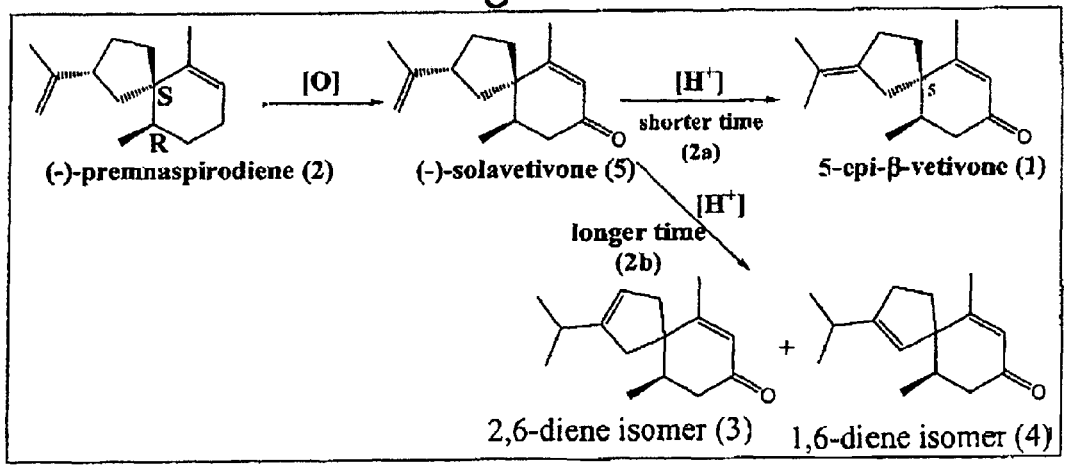
FIG. 5 provides a schematic representation of an oxidation and acid catalyzed isomerization reaction used in the production of 5-epi-β-vetivone (1).

Typically, the allylic carbon oxidation step can be carried out according to a scheme demonstrated in FIG. 5 and described in literature [Hwu, J. R.; Wetzel, J. M., *J. Org. Chem.* (1992), 57(3), 922-928]. Furthermore, the acid catalyzed isomerization step can be carried out according to Scheme (2) below:

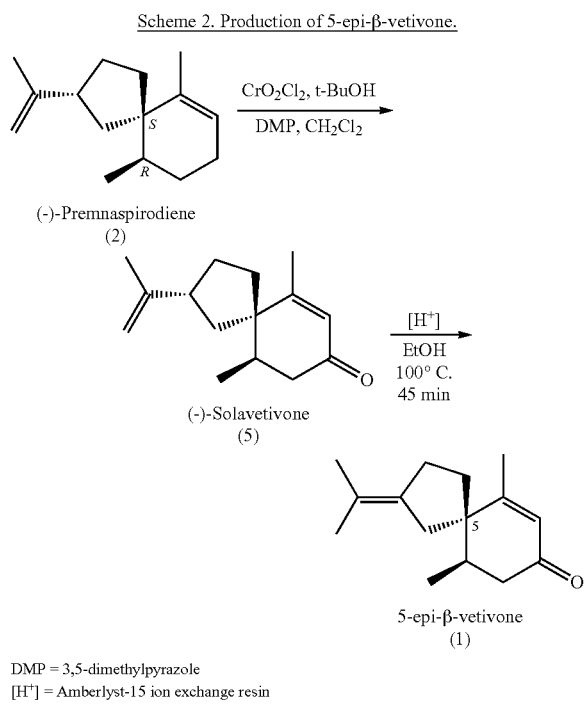

Scheme 2. Production of 5-epi-β-vetivone.

(-)-Premnaspirodiene
(2)

(-)-Solavetivone
(5)

5-epi-β-vetivone
(1)

DMP = 3,5-dimethylpyrazole
[H⁺] = Amberlyst-15 ion exchange resin

The allylic oxidation reaction step may be carried out using metal oxidants, wherein such oxidants include, but are not limited to, chromium, copper, rhodium, cobalt, manganese, or vanadium. Amongst the chromium oxidants, one may use $CrO_3$-pyridine complex, chromium trioxide and 3,5-dimethylpyrazole, chromic acid ($CrO_2Cl_2$) and 3,5-dimethylpyrazole, pyridinium chlorochromate (PCC), pyridinium dichromate (PDC), sodium chromate, sodium dichromate in acetic acid, pyridinium fluorochromate, or 3,5-dimethylpyrazolium fluorochromate(VI). Amongst the copper oxidants, one may use copper(I) bromide, copper(I) iodide, or $Cu(OAc)_2$ and t-BuOOH. Amongst the rhodium oxidants, one may use dirhodium catalysts such as dirhodium tetrakiscaprolactamate ($Rh_2(cap)_4$), $Rh_2(OAc)_4$ or dirhodium tetrakisperfluorobutanoate $Rh_2(pfb)_4$). Amongst the cobalt oxidants, one may use $Co(OAc)_2$ and t-BuOOH. Amongst the manganese oxidants, one may use $Mn(OAc)_2$ and t-BuOOH. Amongst the vanadium oxidants, one may use $V(OAc)_2$ and t-BuOOH. Other, alternative, oxidants are described below.

In a preferred embodiment, the metal oxidant is a chromium or rhodium catalyst such as $CrO_3$-pyridine complex, chromium trioxide and 3,5-dimethylpyrazole, chromic acid ($CrO_2Cl_2$) and 3,5-dimethylpyrazole, pyridinium chlorochromate (PCC), pyridinium dichromate (PDC), sodium chromate, sodium dichromate in acetic acid, pyridinium fluorochromate, 3,5-dimethylpyrazolium fluorochromate(VI), $Rh_2(cap)_4$, $Rh_2(OAc)_4$ or $Rh_2(pfb)_4$.

In a more preferred embodiment, the metal oxidant is a chromium catalyst such as chromic acid ($CrO_2Cl_2$) and 3,5-dimethylpyrazole.

In a preferred embodiment, oxidation of the allylic carbon is performed in a solvent. Typically, the solvent comprises at least one solvent selected from the group consisting of aliphatic alcohols, ether compounds, hydrocarbons, halohydrocarbons, and mixtures thereof.

As used herein, the term "aliphatic alcohol" means a straight-chain or branched-chain aliphatic alcohol of from 1 to 12 carbon atoms, typically of from 1 to 6 carbon atoms. As used herein, the term "ether compound" means a linear or cyclic ether of from 4 to 12 carbon atoms. As used herein, the term "hydrocarbon" means an aliphatic or aromatic hydrocarbon of from 5 to 12 carbon atoms wherein the aliphatic hydrocarbon is a straight-chain or branched-chain alkane. As used herein, the term "halohydrocarbon" means an aliphatic or aromatic halohydrocarbon of from 5 to 12 carbon atoms wherein, when the halohydrocarbon is an aliphatic halohydrocarbon, the hydrocarbon moiety of the halohydrocarbon is a straight-chain or branched-chain alkane, and wherein the halohydrocarbon comprises from 1 to 4 halogens.

In one alternative, the solvent comprises an aliphatic alcohol. Typically, the aliphatic alcohol is selected from the group consisting of methanol, ethanol, n-propanol, and t-butanol. In another alternative, the solvent comprises an ether compound. Typically, the ether compound is selected from the group consisting of ethyl ether, tetrahydrofuran, and dioxane.

In another alternative, the solvent comprises a hydrocarbon. Typically, the hydrocarbon is selected from the group consisting of pentane, hexane, benzene, and toluene.

In another alternative, the solvent comprises a halohydrocarbon. Preferably, the halohydrocarbon is dichloromethane.

Preferably, oxidation of the allylic carbon is performed in a solvent that is a mixture of t-butanol and dichloromethane.

In another alternative, oxidation of the allylic carbon is performed using $CrO_2Cl_2$ as an oxidizing agent and in the presence of 3,5-dimethylpyrazole as a catalyst.

In still another preferred alternative, oxidation of the allylic carbon is performed using t-butyl hydroperoxide and sodium chlorite. Typically, in this alternative, the oxidation is performed in a solvent that is a mixture of acetonitrile, water, and t-butanol; preferably, the mixture of acetonitrile, water, and t-butanol is a 3:1:1 mixture of acetonitrile, water, and t-butanol. In this alternative, preferably, the (−)-premnaspirodiene is first dispersed in a solvent that includes the acetonitrile and water, but not the t-butanol; the t-butyl hydroperoxide is then added, and the reaction heated to 50° C. for 18 h. At this point, the t-butanol is added to the reaction, and the reaction is heated for an additional 16 h at 50° C. (Example 7). The reaction is cooled, poured into a 10% solution of sodium sulfite, and extracted with diethyl ether; the organic layer, containing the desired product, is washed with saturated sodium bicarbonate, dried over sodium sulfate, and then adsorbed onto silica gel. The oxidized product is then purified on a silica gel column and eluted first with 5% ethyl acetate in heptane and then with 10% ethyl acetate in heptane. Details of this procedure are provided in Example 7.

Typically, the acid-catalyzed isomerization step is performed with an acidic isomerization agent. In one alternative, the acidic isomerization agent is selected from the group consisting of mineral acids, organic protonic acids, and Lewis acids. Suitable Lewis acids include, but are not limited to, trifluoroboronetherate, tin chloride, and titanium tetrachloride. Suitable mineral acids include, but are not limited to, phosphoric acid, sulfuric acid, perchloric acid, hydrohalide acids, and heteropolyacids. A suitable heteropolyacid is $H_3[P(W_3O_{10})_4]$. Suitable hydrohalide acids include, but are not limited to, hydrogen chloride, hydrogen bromide, and hydrogen iodide. Suitable organic protonic acids include, but are not limited to, trifluoroacetic acid, acetic acid, and methylsulfonic acid. In one alternative the acidic isomerization agent is a mixture of acetic acid and sulfuric acid.

In the preferred embodiment, the acidic isomerization agent is a solid phase acidic isomerization agent. Solid phase acidic isomerization agents within the scope of the present invention include, but are not limited to, montmorillonite clay, acidic resins, and acidic aluminum oxide. Preferably, the acidic isomerization agent is an acidic resin. Suitable acidic resins include, but are not limited to, Dowex®50 (available from Dow Chemical Co.), Amberlyst® IR-15 (available from Rohm and Haas Co.), and Nafion® perfluorinated resin (available from E.I. du Pont de Nemours & Co., Inc.).

An appropriate range of reaction time and reaction temperature is necessary in order to produce 5-epi-β-vetivone (1) from premnaspirodiene (2) according to Scheme (1) below:

Scheme (1). Effect of Reaction Time on 5-epi-β-vetivone Production.

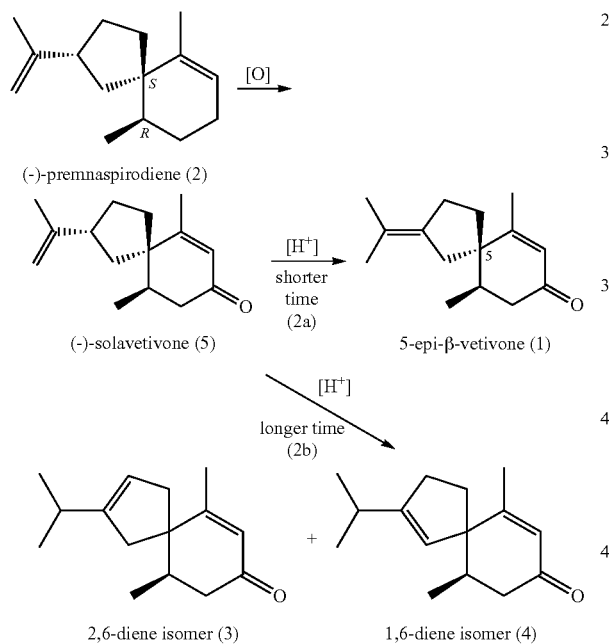

In Scheme (1), the first step, the oxidation of (−)-premnaspirodiene to (−)-solavetivone at the allylic carbon, can be performed by any of the oxidation procedures described above, using metal oxidants or, alternatively, using t-butyl hydroperoxide and sodium chlorite.

A reaction time that is too short will result in low yield of 5-epi-β-vetivone, since not all of the premnaspirodiene will be converted to the desired end-product, 5-epi-β-vetivone. A reaction time that is too long will drive the reaction toward production of a mixture of the 2,6 diene and 1,6 diene isomers as the end-product and no 5-epi-β-vetivone will be produced. Typically, the reaction time preferred for production of 5-epi-β-vetivone is between about 15 minutes and about 120 minutes and the reaction temperature is between about 25 degrees Celsius and about 150 degrees Celsius. More preferably, the reaction time is between about 30 minutes and about 90 minutes. Most preferably, the reaction time is between about 40 minutes and about 60 minutes. Appropriate reaction temperature is similarly important. In the preferred embodiment, the reaction temperature is between about 25 degrees Celsius and about 150 degrees Celsius. More preferably, the reaction temperature is between about 50 degrees Celsius and about 125 degrees Celsius. Most preferably, the reaction temperature is between about 75 degrees Celsius and about 105 degrees Celsius.

In another embodiment the present invention describes a method for synthesizing a mixture of 2-isopropyl-6,10-dimethyl-spiro[4.5]deca-2,6-dien-8-one (3) and 2-isopropyl-6,10-dimethyl-spiro[4.5]deca-1,6-dien-8-one (4) comprising the steps of:

(1) subjecting (−)-premnaspirodiene (2) to oxidation of an allylic carbon to form (−)-solavetivone (5); and (2) subjecting the (−)-solavetivone (5) formed in step (1) to acid-catalyzed isomerization to form the mixture of 2-isopropyl-6,10-dimethyl-spiro[4.5]deca-2,6-dien-8-one (3) and 2-isopropyl-6,10-dimethyl-spiro[4.5]deca-1,6-dien-8-one (4);

wherein time and temperature conditions for step (ii) are such that the predominant product is a mixture of 2-isopropyl-6,10-dimethyl-spiro[4.5]deca-2,6-dien-8-one (3) and 2-isopropyl-6,10-dimethyl-spiro[4.5]deca-1,6-dien-8-one (4).

Figure 6:
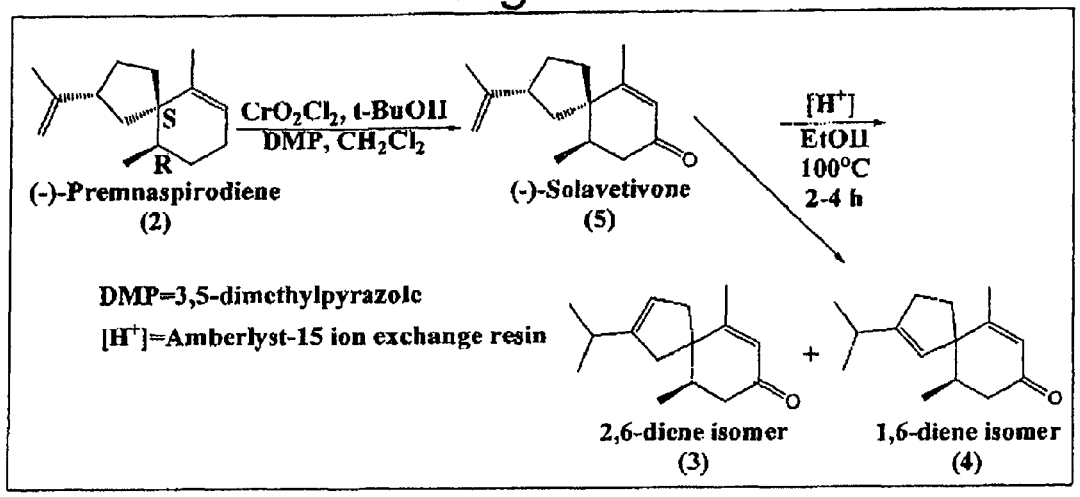
FIG. 6 provides a schematic representation of an oxidation and acid catalyzed isomerization reaction used in the production of 2-isopropyl-6,10-dimethyl-spiro[4.5]deca-2,6-dien-8-one (3) and 2-isopropyl-6,10-dimethyl-spiro[4.5]deca-1,6-dien-8-one (4).

Typically, the allylic carbon oxidation step can be carried out according to a scheme demonstrated in FIG. 6 and described in literature [Hwu, J. R.; Wetzel, J. M., *J. Org. Chem.* (1992), 57(3), 922-928]. Furthermore, the acid catalyzed isomerization step can be carried out according to Scheme (3) below:

Scheme 3. Production of 2,6-diene isomer and 1,6-diene isomer

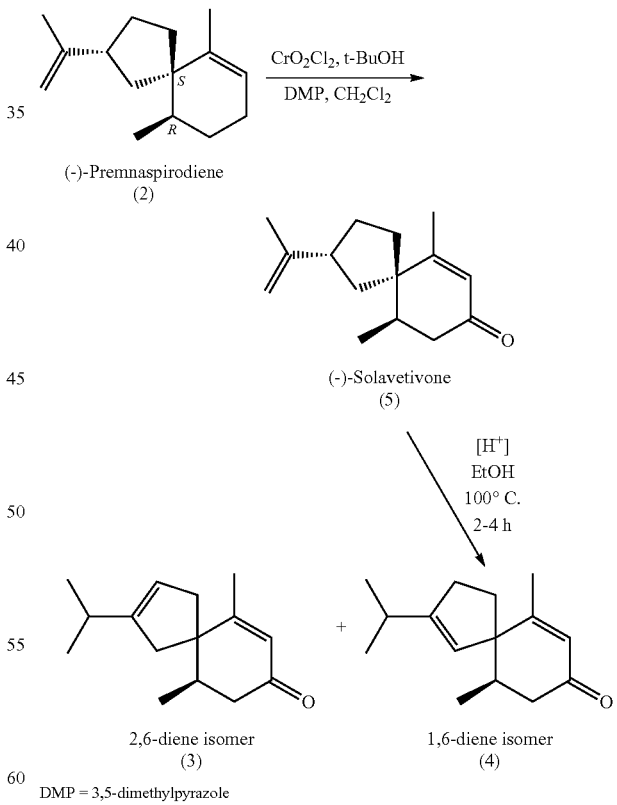

DMP = 3,5-dimethylpyrazole
[H⁺] = Amberlyst-15 ion exchange resin

Typically, oxidation of the allylic carbon is performed using $CrO_2Cl_2$ as an oxidizing agent. In the preferred embodiment, the oxidation step is performed in a solvent. Preferably, the oxidation step is performed in a solvent comprising at least one solvent selected from the group consisting of aliphatic alcohols, ether compounds, hydrocarbons, halohydrocarbons, and mixtures thereof. Alternatively, a solvent comprising an aliphatic alcohol may be used. For example, the oxidation step may be performed in an aliphatic alcohol selected from the group including, but not limited to, methanol, ethanol, n-propanol, and t-butanol. Alternatively, a solvent comprising an ether compound may be used. Suitable solvents comprising an ether compound may be selected from the group including, but not limited to, ethyl ether, tetrahydrofuran, and dioxane. In another alternative, oxidation step may be performed in a solvent comprising a hydrocarbon. Suitable solvents comprising a hydrocarbon may be selected from the group including, but not limited to, pentane, hexane, benzene, and toluene. In another alternative, oxidation step may be performed in a solvent comprising a halohydrocarbon. For example, dichloromethane may be used as a solvent. Alternatively, oxidation step may be performed in a solvent that is a mixture of t-butanol and dichloromethane.

In another alternative, oxidation of the allylic carbon is performed using $CrO_2Cl_2$ as an oxidizing agent and in the presence of 3,5-dimethylpyrazole as a catalyst. Other oxidizing agents and catalysts within the scope of the present invention will be known to one of reasonable skill in the art. In another alternative, the acid-catalyzed isomerization step is performed with an acidic isomerization agent. Preferably, an acidic isomerization agent is selected from the group including, but not limited to, mineral acids, organic protonic acids, and Lewis acids. Typically, the acidic isomerization agent is a mineral acid selected from the group including, but not limited to, phosphoric acid, sulfuric acid, perchloric acid, hydrohalide acids, and heteropolyacids. Preferably, the acidic isomerization agent is a heteropolyacid. Alternatively, the acidic isomerization agent is $H_3[F(W_3O_{10})_4]$. In another alternative, the acidic isomerization agent is a hydrohalide acid selected from the group including, but not limited to, hydrogen chloride, hydrogen bromide, and hydrogen iodide. In another alternative, the acidic isomerization agent is a carboxylic acid or a sulfonic acid. Other examples of a suitable acidic isomerization agent include, but are not limited to, trifluoroacetic acid, acetic acid, and methylsulfonic acid. A mixture of acetic acid and sulfuric acid may also be used as an acidic isomerization agent. Other acidic mixtures within the scope of the present invention will be known to one of reasonable skill in the art.

In a preferred embodiment, a solid phase acidic isomerization agent is used. For example, suitable solid phase acidic isomerization agents include, but are not limited to, montmorillonite clay, acidic resins, Dowex®50, Amberlyst® IR-15, and Nafion® perfluorinated resin. Additional examples of suitable acidic isomerization agents include, but are not limited to, acidic aluminum oxide, trifluoroboronetherate, tin chloride, and titanium tetrachloride.

An appropriate range of reaction time and reaction temperature is necessary in order to produce a mixture of 2-isopropyl-6,10-dimethyl-spiro[4.5]deca-2,6-dien-8-one (3) and 2-isopropyl-6,10-dimethyl-spiro[4.5]deca-1,6-dien-8-one (4) from premnaspirodiene (2) according to Scheme (1) below:

Scheme (1). Effect of Reaction Time on Diene Isomer Production.

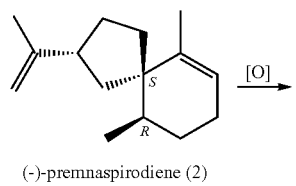

(-)-premnaspirodiene (2)

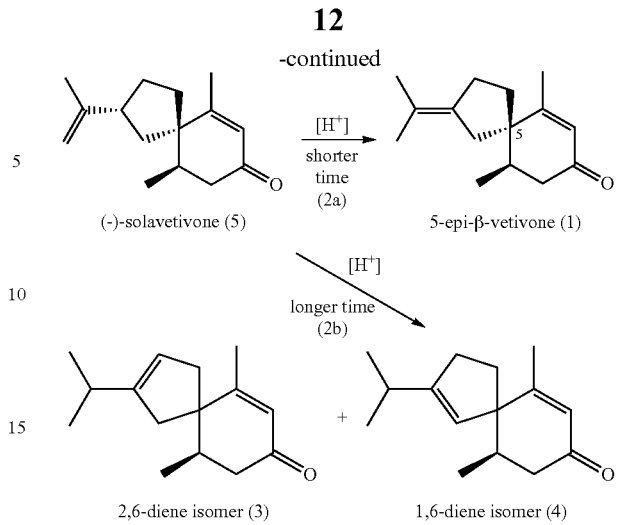

A reaction time that is too short will result in low yield of the mixture of 2,6 diene and 1,6 diene isomers, since not all of the premnaspirodiene will be converted to the desired end-product. A reaction time that is too long is uneconomical and presents problems for industrial scale production of the desired end product. Typically, the reaction time preferred for production of the mixture of 2,6 diene and 1,6 diene isomers is between about 1 hour and about 96 hours and the reaction temperature is between about 25 degrees Celsius and about 150 degrees Celsius. More preferably, the reaction time is between about 2 hours and about 24 hours. Most preferably, the reaction time is between about 2 hours and about 6 hours. Appropriate reaction temperature is similarly important. In the preferred embodiment, the reaction temperature is between about 25 degrees Celsius and about 150 degrees Celsius. More preferably, the reaction temperature is between about 50 degrees Celsius and about 125 degrees Celsius. Most preferably, the reaction temperature is between about 75 degrees Celsius and about 105 degrees Celsius. In the preferred embodiment, the reaction time is between about 1 hour and about 96 hours and reaction temperature is between about 25 degrees Celsius and about 150 degrees Celsius.

In another embodiment the present invention describes a method for synthesizing 2-isopropyl-6,10-dimethyl-spiro [4.5]deca-2,6-dien-8-one (3) and 2-isopropyl-6,10-dimethyl-spiro[4.5]deca-1,6-dien-8-one (4) comprising the steps of:

(1) subjecting (−)-premnaspirodiene (2) to oxidation of an allylic carbon to form (−)-solavetivone (5); and (2) subjecting the (−)-solavetivone (5) formed in step (1) to acid-catalyzed isomerization to form the mixture of 2-isopropyl-6,10-dimethyl-spiro[4.5]deca-2,6-dien-8-one (3) and 2-isopropyl-6,10-dimethyl-spiro[4.5]deca-1,6-dien-8-one (4).

In this alternative, the time and temperature conditions for step (2) are such that the predominant product is a mixture of 2-isopropyl-6,10-dimethyl-spiro[4.5]deca-2,6-dien-8-one (3) and 2-isopropyl-6,10-dimethyl-spiro[4.5]deca-1,6-dien-8-one (4). In this alternative, the method can further comprise the step of separating 2-isopropyl-6,10-dimethyl-spiro[4.5] deca-2,6-dien-8-one (3) and 2-isopropyl-6,10-dimethyl-spiro[4.5]deca-1,6-dien-8-one (4) from the mixture of 2-isopropyl-6,10-dimethyl-spiro[4.5]deca-2,6-dien-8-one (3) and 2-isopropyl-6,10-dimethyl-spiro[4.5]deca-1,6-dien-8-one (4) in order to produce the two positional isomers individually. Typically, the separation step is performed by a method selected from the group consisting of thin-layer chromatography, column chromatography, gas chromatography, and countercurrent distribution. Other separation steps within the scope of the present invention will be known to one of reasonable skill in the art.

In another embodiment the present invention describes a substantially purified and isolated mixture of 2-isopropyl-6,10-dimethyl-spiro[4.5]deca-2,6-dien-8-one (3) and 2-isopropyl-6,10-dimethyl-spiro[4.5]deca-1,6-dien-8-one (4). This substantially purified and isolated mixture is prepared by the method described above and includes both positional isomers. As used herein with reference to this substantially purified and isolated mixture, the term "substantially purified and isolated" means that the mixture is substantially free of side products and unreacted components, although solvents and other inert substances may remain. Although a specific degree of purity is not intended by the use of the term "substantially purified and isolated," typically, when solvents and other inert substances are removed from consideration of purity, the mixture forms at least about 75% of the compounds present. More typically, the mixture forms at least about 85% of the compounds present. Preferably, the mixture forms at least about 95% of the compounds present. More preferably, the mixture forms at least 97.5% of the compounds present. Still more preferably, the mixture forms at least 99% of the compounds present. Still more preferably, the mixture forms at least 99.5% of the compounds present.

Figure 1:
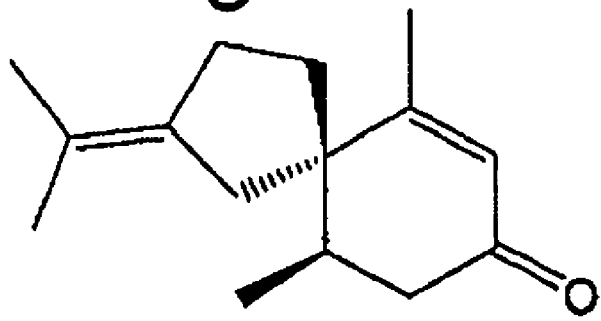
FIG. 1 depicts the structural formula of 5-epi-β-vetivone (1).
Figure 2:
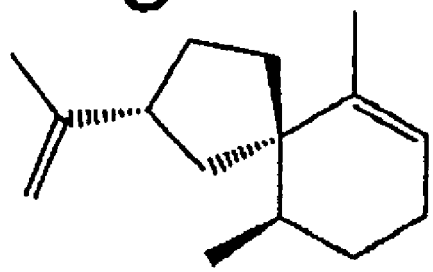
FIG. 2 depicts the structural formula of premnaspirodiene (2).
Figure 3A:
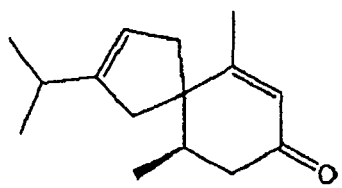
FIG. 3A depicts the structural formula of the 2,6-diene isomer.

In another embodiment the present invention describes the substantially purified and isolated compound 2-isopropyl-6,10-dimethyl-spiro[4.5]deca-2,6-dien-8-one represented by FIG. 3A, substantially free of 2-isopropyl-6,10-dimethyl-spiro[4.5]deca-1,6-dien-8-one. As used herein with respect to this compound and with respect to the other positional isomer 2-isopropyl-6,10-dimethyl-spiro[4.5]deca-1,6-dien-8-one, below, the term "substantially purified and isolated" means that the preparation is substantially free of side products and unreacted components, although solvents and other inert substances may remain. Although a specific degree of purity is not intended by the use of the term "substantially purified and isolated," typically, when solvents and other inert substances are removed from consideration of purity, the desired compound (i.e., 2-isopropyl-6,10-dimethyl-spiro[4.5]deca-2,6-dien-8-one) forms at least about 75% of the compounds present. More typically, the desired compound forms at least about 85% of the compounds present. Preferably, the desired compound forms at least about 95% of the compounds present. More preferably, the desired compound forms at least 97.5% of the compounds present. Still more preferably, the desired compound forms at least 99% of the compounds present. Still more preferably, the desired compound forms at least 99.5% of the compounds present.

Figure 3B:
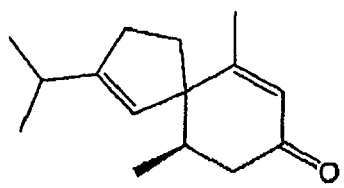
FIG. 3B depicts the structural formula of the 1,6-diene isomer.
Figure 4:
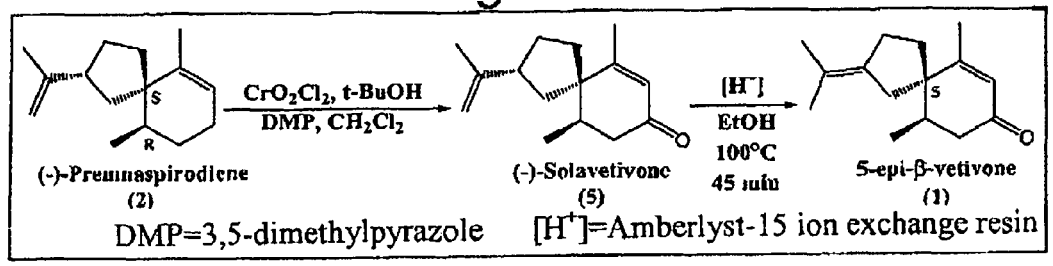
FIG. 4 provides a schematic representation of an oxidation and acid catalyzed isomerization reaction used in the production methods of the present invention.

In another embodiment the present invention describes the substantially purified and isolated compound 2-isopropyl-6,10-dimethyl-spiro[4.5]deca-1,6-dien-8-one represented by FIG. 3B, substantially free of 2-isopropyl-6,10-dimethyl-spiro[4.5]deca-2,6-dien-8-one. The term "substantially purified and isolated" with respect to this compound is as defined above with respect to the substantially purified and isolated compound 2-isopropyl-6,10-dimethyl-spiro[4.5]deca-2,6-dien-8-one.

In another embodiment the present invention describes a method for producing (−)-premnaspirodiene (2) from a terpene substrate, comprising the steps of:

(1) providing the terpene substrate to a host cell transformed or transfected with a vector comprising a sequence encoding a *Hyoscyamus muticus* premnaspirodiene synthase gene;

(2) culturing the host cell under conditions suitable to produce (−)-premnaspirodiene from the terpene substrate; and (3) isolating the (−)-premnaspirodiene.

Suitable production hosts may include, but are not limited to, any organism capable of expressing the genes required for the premnaspirodiene production. Typically, the host cell will be a microorganism cell or a plant cell. Other suitable host cells within the scope of the present invention will be known to one of reasonable skill in the art.

Microorganism host cells useful in the present invention for the production of premnaspirodiene may include, but are not limited to, bacteria, such as the enteric bacteria (*Escherichia* and *Salmonella* for example) as well as *Bacillus*, *Acinetobacter*, *Streptomyces*, *Methylobacter*, *Rhodococcus* and *Pseudomonas*; Cyanobacteria, such as *Rhodobacter* and *Synechocystis*; yeasts, such as *Saccharomyces*, *Zygosaccharomyces*, *Kluyveromyces*, *Candida*, *Hansenula*, *Debaryomyces*, *Mucor*, *Pichia* and *Torulopsis*; and filamentous fungi such as *Aspergillus* and *Arthrobotrys*, and algae for example. Preferably, the host cell is a eukaryotic cell. More preferably, the host cell is a yeast cell, which is a eukaryotic microorganism host cell. Most preferably, the host cell is a *Saccharomyces cerevisiae* cell.

Microbial expression systems and expression vectors containing regulatory sequences that direct high level expression of foreign proteins are well known to those skilled in the art. These expression systems and expression vectors are known both for prokaryotic organisms such as bacteria and for eukaryotic organisms such as yeast. Similarly, vectors or cassettes useful for the transformation of suitable microbial host cells are well known in the art. These vectors and cassettes are known both for prokaryotic organisms such as bacteria and for eukaryotic organisms such as yeast. Typically, the vector or cassette contains sequences directing expression of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination.

The *Hyoscyamus muticus* premnaspirodiene synthase gene is described in K. Back & J. Chappell, "Cloning and Bacterial Expression of a Sesquiterpene Cyclase from *Hyoscyamus muticus* and Its Molecular Comparison to Related Terpene Cyclases," *J. Biol. Chem.* 270: 7375-7381 (1995); K. Back & J. Chappell, "Identifying Functional Domains Within Terpene Cyclases Using a Domain-Swapping Strategy, *Proc. Natl. Acad. Sci. USA* 93: 6841-6845 (1996); and B. T. Greenhagen et al., "Identifying and Manipulating Structural Determinates Linking Catalytic Specificities in Terpene Synthases," *Proc. Natl. Acad. Sci. USA* 103: 9826-9831 (2006), all of which are incorporated by these references, and, as used herein, typically includes nucleic acid sequences encoding amino acid sequences identified in these references as part of active domains, including catalytic domains and domains responsible for selectivity of the synthase reaction. As used herein, recitation of a nucleic acid sequence encoding a specified amino acid sequence includes all possible codons encoding that amino acid sequence in the absence of evidence suggesting that any possible codon or combination of codons would be nonfunctional in the step of either transcription of the DNA sequence or translation of the resulting mRNA.

Initiation control regions or promoters, which are useful to drive expression of the relevant genes in the desired host cell are numerous and familiar to those skilled in the art. Termination control regions may also be derived from various genes native to the preferred hosts.

Expression of cloned heterologous genes in yeast cells, particularly cells of *S. cerevisiae*, is described in the following references, all of which are incorporated herein by these references: S. D. Emr, "Heterologous Gene Expression in Yeast," Meth. Enzymol. 185: 231-233 (1991), is a general overview of expression in yeast, including the possibility of exploiting protein secretion and modification in yeast and achieving stability of expressed proteins. A. B. Rose & J. R. Broach, "Propagation and Expression of Cloned Genes in Yeast: 2-μm Circle-Based Vectors, Meth. Enzymol. 185: 234-279 (1991), describes the use of 2-μm circle-based vectors for transfection of genes into yeast and for expression of heterologous genes in yeast, including standard 2-μm circle-based vectors, vectors for high copy propagation, vectors for expression of cloned genes in yeast, and vectors for specialized applications. T. Stearns et al., "Manipulating Yeast Genome Using Plasmid Vectors," Meth. Enzymol. 185: 280-297 (1991), describes the use of yeast vector systems and components, the use of homologous recombination to integrate plasmids into the yeast host genome, and the use of centromere plasmids. L. M. Mylin et al., "Regulated GAL4 Expression Cassette Providing Controllable and High-Level Output from High-Copy Galactose Promoters in Yeast," Meth. Enzymol. 185: 297-308 (1991), describes the use of galactose-inducible promoters to provide high levels of production of cloned proteins in yeast. V. L. Price et al., "Expression of Heterologous Proteins in *Saccharomyces cerevisiae* Using the ADH2 Promoter," Meth. Enzymol. 185: 308-318 (1991), describes the use of the glucose-repressible ADH2 promoter to provide controllable, high level expression of cloned proteins in yeast. T. Etcheverry, "Induced Expression Using Yeast Copper Metallothionein Promoter," Meth. Enzymol. 185: 319-329 (1991), describes the use of the yeast CUP1 promoter to drive controllable expression of cloned genes in yeast. S. M. Kingsman et al., "High-Efficiency Yeast Expression Vectors Based on the Promoter of the Phosphoglycerate Kinase Gene," Meth. Enzymol. 185: 329-341 (1991), describes the use of the yeast PGK promoter to drive controllable expression of cloned genes in yeast. S. Rosenberg et al., "Glyceraldehyde-3-Phosphate Dehydrogenase-Derived Expression Cassettes for Constitutive Synthesis of Heterologous Proteins," Meth. Enzymol. 185: 341-350 (1991), describes the use of expression cassette plasmids utilizing the strong GAPDH-491 promoter for high levels of heterologous protein production in yeast. A. Z. Sledziewski et al., "Superimposition of Temperature Regulation on Yeast Promoters," Meth. Enzymol. 185: 351-366 (1991), describes the construction of temperature-regulated variants of two strong yeast promoters, TPI1 and ADH2, and the use of these promoters for regulation of expression and thus regulation of the extent of glycosylation of proteins secreted by yeast. T. F. Donahue & A. M. Cigan, "Sequence and Structural Requirements for Efficient Translation in Yeast," Meth. Enzymol. 185: 366-372 (1991), describes the significance of codon usage variations between yeast and higher eukaryotes and the selection of efficient leader sequences. E. W. Jones, "Vacuolar Proteases in Yeast *Saccharomyces cerevisiae*," Meth. Enzymol. 185: 372-386 (1991), describes the elimination of vacuolar protease activity in yeast to maximize the yield of protein production from cloned genes. K. D. Wilkinson, "Detection and Inhibition of Ubiquitin-Dependent Proteolysis," Meth. Enzymol. 185: 387-397 (1991), describes methods for preventing ubiquitin-dependent protein degradation in yeast, again to maximize the yield of protein production from cloned genes. R. L. Kendall et al., "Cotranslational Amino-Terminal Processing," Meth. Enzymol. 185: 398-407 (1991), describes the cotranslational processing events that occur in yeast at the amino-termini of nascent polypeptide genes and their effects on heterologous gene expression and protein stability. A. J. Brake, "α-Factor Leader-Directed Secretion of Heterologous Proteins from Yeast," Meth. Enzymol. 185: 408-421 (1991), describes expression systems based on the yeast α-factor leader. R. A. Hitzeman et al., "Use of Heterologous and Homologous Signal Sequences for Secretion of Heterologous Proteins from Yeast," Meth. Enzymol. 185: 421-440 (1991), describes the use of both heterologous and homologous signal sequences for the production and secretion of heterologous gene products in yeast. V. Chisholm et al., "Molecular and Genetic Approach to Enhancing Protein Secretion," Meth. Enzymol. 185: 471-482 (1991), describes the use of an enhanced secretion phenotype occurring among drug-resistant yeast mutants to maximize secretion of cloned proteins in yeast.

General molecular biological techniques of gene cloning, site-directed mutagenesis, and fusion protein construction can be used to provide nucleic acid segments that include therein the *Hyoscyamus muticus* premnaspirodiene synthase gene. Typically, the nucleic acid segments are DNA nucleic acid segments. Typically, as described above, the *Hyoscyamus muticus* premnaspirodiene synthase gene is operatively linked to at least one nucleic acid expression control element, such as, but not limited to, a promoter, an enhancer, or a site capable of binding a repressor or activator. Such nucleic acid expression control elements are well known in the art. Typically, as described above, the *Hyoscyamus muticus* premnaspirodiene synthase gene is included in a vector and, as such, is again operatively linked to at least one nucleic acid expression control element. Site-directed mutagenesis can be used, for example, to provide optimum codon selection for expression in *S. cerevisiae*, as described above. The *Hyoscyamus muticus* premnaspirodiene synthase gene can, in one alternative, be expressed in the form of a nucleic acid segment encoding a fusion protein, such as a purification tag or other detectable protein domain.

Where commercial production of premnaspirodiene is desired, a variety of fermentation methodologies may be applied. For example, large scale production may be effected by either batch or continuous fermentation. A classical batch fermentation is a closed system where the composition of the media is set at the beginning of the fermentation and not subject to artificial alterations during the fermentation. Thus, at the beginning of the fermentation the medium is inoculated with the desired microorganism or microorganisms and fermentation is permitted to occur without further addition of nutrients. Typically, the concentration of the carbon source in a batch fermentation is limited, and factors such as pH and oxygen concentration are controlled. In batch systems the metabolite and biomass compositions of the system change constantly up to the time the fermentation is stopped. Within batch cultures cells typically modulate through a static lag phase to a high growth log phase and finally to a stationary phase where growth rate is diminished or halted. If untreated, cells in the stationary phase will eventually die.

A variation on the standard batch system is the Fed-Batch system. Fed-Batch fermentation processes are also suitable for use in the present invention and comprise a typical batch system with the exception that nutrients are added as the fermentation progresses. Fed-Batch systems are useful when catabolite repression is apt to inhibit the metabolism of the cells and where it is desirable to have limited amounts of substrate in the medium. Also, the ability to feed nutrients will often result in higher cell densities in Fed-Batch fermentation processes compared to Batch fermentation processes. Factors such as pH, dissolved oxygen, nutrient concentrations, and the partial pressure of waste gases such as $CO_2$ are generally measured and controlled in Fed-Batch fermentations. Batch and Fed-Batch fermentations are common and well known in the art and examples may be found in Brock, T. D.; Biotechnology: A Textbook of Industrial Microbiology, 2nd ed.; Sinauer Associates: Sunderland, Mass., 1989; or Deshpande, M. V. Appl. Biochem. Biotechnol. 36:227 (1992), herein incorporated by reference.

Commercial production of premnaspirodiene may also be accomplished with continuous fermentation. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in their log phase of growth. Continuous fermentation allows for modulation of any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by the medium turbidity, is kept constant. Continuous systems strive to maintain steady state growth conditions and thus the cell loss due to the medium removal must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

In the preceding embodiments, typically the terpene substrate is farnesyl diphosphate. Preferably, the host cell is a yeast cell that overproduces farnesyl diphosphate. Most preferably, the host cell is a *Saccharomyces cerevisiae* cell that overproduces farnesyl diphosphate. Other suitable host cells and substrates within the scope of the present invention will be known to one of reasonable skill in the art.

Typically, the step of isolating the premnaspirodiene produced by the host cell is performed by: (i) sequestering the premnaspirodiene by binding it to a hydrophobic resin; (ii) and isolating the premnaspirodiene from the hydrophobic resin. Preferably, the hydrophobic resin is Amberlite® XAD-16 hydrophobic resin. Other hydrophobic resins within the scope of the present invention will be known to one of reasonable skill in the art.

Typically, premnaspirodiene is isolated from the hydrophobic resin by methanol extraction. Other methods of isolating premnaspirodiene that are within the scope of the present invention will be known to one of reasonable skill in the art.

In an alternative, a two-phase system can be used with a non-polar solvent, substantially immiscible with an aqueous phase, added to the fermentation broth and the premnaspirodiene removed from the non-polar phase by distillation. A preferred non-polar solvent is an oil. A particularly preferred oil is a vegetable oil such as soybean oil. Alternative non-polar solvents include, but are not limited to, high molecular weight aliphatic hydrocarbons such as, but not limited to, dodecane, tridecane, tetradecane, pentadecane, and hexadecane; either straight-chain or branched-chain isomers can be used; these high-molecular weight aliphatic hydrocarbons are optionally substituted with one or more hydroxy or halogen substituents as long as the substituted hydrocarbon remains substantially immiscible with the aqueous phase.

Others have reported the use of two-phase systems in bacterial whole cell transformations (R. J. Sowden et al., "Biotransformation of the Sesquiterpene (+)-Valencene by Cytochrome $P450_{cam}$ and $P450_{BM-3}$," Org. Biomol. Chem. 3: 57-64 (2005)) and in yeast fermentations (A.-L. Lindahl et al., "Production of Artemisinin Precursor Amorpha-1,4-diene by Engineered *Saccharomyces cerevisiae*," Biotechnol. Lett. 28: 571-580 (2006)). In those cases the hydrocarbons hexadecane and dodecane were used.

In another embodiment the present invention describes a method for synthesizing 5-epi-β-vetivone (1) comprising the steps of:

(1) providing a terpene substrate to a host cell transformed or transfected with a vector comprising a sequence encoding a *Hyoscyamus muticus* premnaspirodiene synthase gene;

(2) culturing the host cell under conditions suitable to produce (−)-premnaspirodiene from the terpene substrate;

(3) isolating the (−)-premnaspirodiene (2);

(4) subjecting the isolated (−)-premnaspirodiene (2) to oxidation of an allylic carbon to form (−)-solavetivone (5); and (5) subjecting the (−)-solavetivone (5) formed in step (4) to acid-catalyzed isomerization to form 5-epi-β-vetivone (1); wherein time and temperature conditions for step (5) are such that the predominant product is 5-epi-β-vetivone (1).

As used herein, the term "providing a terpene substrate" can include: (1) provision of an extraneous terpene substrate to the host cells; or (2) having the host cells themselves synthesize the terpene substrate so that the terpene substrate can be converted into the (−)-premnaspirodiene (2). Typically, the host cells synthesize the terpene substrate.

In another embodiment the present invention describes a method for synthesizing a mixture of 2-isopropyl-6,10-dimethyl-spiro[4.5]deca-2,6-dien-8-one (3) and 2-isopropyl-6,10-dimethyl-spiro[4.5]deca-1,6-dien-8-one (4) comprising the steps of (1) providing a terpene substrate to a host cell transformed or transfected with a vector comprising a sequence encoding a *Hyoscyamus muticus* premnaspirodiene synthase gene as described above;

(2) culturing the host cell under conditions suitable to produce (−)-premnaspirodiene from the terpene substrate;

(3) isolating the (−)-premnaspirodiene (2);

(4) subjecting the isolated (−)-premnaspirodiene (2) to oxidation of an allylic carbon to form (−)-solavetivone (5); and (5) subjecting the (−)-solavetivone (5) formed in step (4) to acid-catalyzed isomerization to form the mixture of 2-isopropyl-6,10-dimethyl-spiro[4.5]deca-2,6-dien-8-one (3) and 2-isopropyl-6,10-dimethyl-spiro[4.5]deca-1,6-dien-8-one (4);

wherein time and temperature conditions for step (5) are such that the predominant product is the mixture of 2-isopropyl-6,10-dimethyl-spiro[4.5]deca-2,6-dien-8-one (3) and 2-isopropyl-6,10-dimethyl-spiro[4.5]deca-1,6-dien-8-one (4).

Similar methods, with an additional step of isolating the positional isomers, can be used to synthesize 2-isopropyl-6,10-dimethyl-spiro[4.5]deca-2,6-dien-8-one or 2-isopropyl-6,10-dimethyl-spiro[4.5]deca-1,6-dien-8-one.

In general, the method for synthesizing 2-isopropyl-6,10-dimethyl-spiro[4.5]deca-2,6-dien-8-one comprises the steps of:

(1) providing a terpene substrate to a host cell transformed or transfected with a vector comprising a sequence encoding a *Hyoscyamus muticus* premnaspirodiene synthase gene;

(2) culturing the host cell under conditions suitable to produce (−)-premnaspirodiene from the terpene substrate; and (3) isolating the (−)-premnaspirodiene;

(4) subjecting the isolated (−)-premnaspirodiene to oxidation of an allylic carbon to form (−)-solavetivone; and (5) subjecting the (−)-solavetivone formed in step (4) to acid-catalyzed isomerization to form a mixture of 2-isopropyl-6,10-dimethyl-spiro[4.5]deca-2,6-dien-8-one and 2-isopropyl-6,10-dimethyl-spiro[4.5]deca-1,6-dien-8-one; wherein time and temperature conditions for step (5) are such that the predominant product is the mixture of 2-isopropyl-6,10-dimethyl-spiro[4.5]deca-2,6-dien-8-one and 2-isopropyl-6,10-dimethyl-spiro[4.5]deca-1,6-dien-8-one; and (6) isolating the 2-isopropyl-6,10-dimethyl-spiro[4.5]deca-2,6-dien-8-one from the mixture of 2-isopropyl-6,10-dimethyl-spiro[4.5]deca-2,6-dien-8-one and 2-isopropyl-6,10-dimethyl-spiro[4.5]deca-1,6-dien-8-one formed in step (5) by a method selected from the group consisting of thin-layer chromatography, column chromatography, gas chromatography, and countercurrent distribution.

In general, the method for synthesizing 2-isopropyl-6,10-dimethyl-spiro[4.5]deca-1,6-dien-8-one comprises the steps of:

(1) providing a terpene substrate to a host cell transformed or transfected with a vector comprising a sequence encoding a *Hyoscyamus muticus* premnaspirodiene synthase gene;

(2) culturing the host cell under conditions suitable to produce (−)-premnaspirodiene from the terpene substrate; and (3) isolating the (−)-premnaspirodiene;

(4) subjecting the isolated (−)-premnaspirodiene to oxidation of an allylic carbon to form (−)-solavetivone; and (5) subjecting the (−)-solavetivone formed in step (4) to acid-catalyzed isomerization to form a mixture of 2-isopropyl-6,10-dimethyl-spiro[4.5]deca-2,6-dien-8-one and 2-isopropyl-6,10-dimethyl-spiro[4.5]deca-1,6-dien-8-one; wherein time and temperature conditions for step (5) are such that the predominant product is the mixture of 2-isopropyl-6,10-dimethyl-spiro[4.5]deca-2,6-dien-8-one and 2-isopropyl-6,10-dimethyl-spiro[4.5]deca-1,6-dien-8-one; and (6) isolating the 2-isopropyl-6,10-dimethyl-spiro[4.5]deca-1,6-dien-8-one from the mixture of 2-isopropyl-6,10-dimethyl-spiro[4.5]deca-2,6-dien-8-one and 2-isopropyl-6,10-dimethyl-spiro[4.5]deca-1,6-dien-8-one formed in step (5) by a method selected from the group consisting of thin-layer chromatography, column chromatography, gas chromatography, and countercurrent distribution.

The present invention also includes a fragrance composition with a compound having the structure:

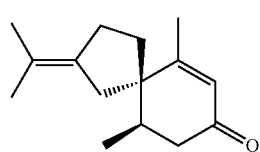

Formula (1)

in an amount effective to impart a fragrance. In one aspect, the compound of the fragrance composition is present in an amount of at least 0.01% by weight. In another aspect, the fragrance composition comprises an amount of the compound of Formula (1) effective to impart fragrance in combination with conventional fragrance ingredients.

Another object of the present invention is a perfumed product comprising a compound having the structure of Formula (1). The perfumed product can be a household product, such as, for example, a solid or liquid detergent, a fabric softener, an air freshener, a fabric refresher, an ironing water, a paper, a wipe or a bleach. The perfumed product can be a cosmetic product or a body care product, for example a perfume, a cologne or after-shave lotion, a perfumed soap, a shower or bath salt, mousse, oil or gel, a hygiene product, a hair care product, a shampoo, a deodorant or antiperspirant.

The present invention can be a perfuming composition containing the compound of Formula (1) in an amount sufficient to give a fragrance to the composition. In one embodiment, the perfuming composition can additionally contain at least one perfumery adjuvant.

Another aspect of the present invention is a fragrance application comprising a compound of Formula (1). The fragrance application can be, for example, a household product such as laundry product, a solid or liquid detergent, a fabric softener, an air freshener, a fabric refresher, an ironing water, a paper, a wipe or a bleach. In another aspect, the fragrance application can be a cosmetic product or body care product such as a perfume, a cologne or after-shave lotion, a perfumed soap, a shower or bath salt, mousse, oil or gel, a hygiene product, a hair care product, a shampoo, a deodorant or antiperspirant.

The invention also includes methods of imparting a woody, grapefruit, or vetivent odor to a fragrance or fragrance composition by providing the compound of Formula (1) to the fragrance.

Methods of the invention include imparting, improving, enhancing or modifying a fragrance formulation through the addition of an olfactory acceptable amount of Formula (1). The olfactory acceptable amount can be from about 0.005 to about 10 weight percent of the fragrance formulation. In one aspect, the olfactory acceptable amount is from about 0.5 to about 8 weight percent of the fragrance formulation. In another aspect, the method of claim 18, wherein the olfactory acceptable amount is from about 1 to about 7 weight percent of the fragrance formulation.

As mentioned above, the invention provides for the synthesis of compounds to be used as a perfuming ingredient. In another embodiment, the invention describes a method to confer, enhance, improve or modify the odor properties of a perfuming composition or of a perfumed article. The method comprises adding an effective amount of the fragrant component described by the formulas to said perfumed compositions or article.

The compounds, which are perfuming compositions that can be advantageously employed as perfuming ingredients, are also an object of the present invention. The fragrance or perfume composition can also contain additional ingredients such as a perfumery carrier, a perfumery base; or one or more one perfumery adjuvants. Examples of fragrance and perfuming compositions can be found in, for example, Arctander, S., Perfume and Flavor Chemicals (Montclair, N.J., 1969), Arctander, S., Perfume and Flavor Materials of Natural Origin (Elizabeth, N.J., 1960) and in "Flavor and Fragrance Materials—1991," Allured Publishing Co. Wheaton, Ill. USA, which are herein incorporated by reference.

The terms "fragrance" or "perfume" means a discernible odor at normal room temperature (about 25° C.) that is generally regarded as interesting, pleasant or attractive. The term "perfumery carrier" means a material which is practically neutral from a perfumery point of view, i.e. that does not significantly alter the organoleptic properties of perfuming ingredients. The carrier may be a liquid or a solid.

A liquid carrier may be, for example, an emulsifying system, i.e. a solvent and a surfactant system, or a solvent commonly used in perfumery. A solvent can be, for example, a dipropyleneglycol, diethyl phthalate, isopropyl myristate, benzyl benzoate, 2-(2-ethoxyethoxy)-1-ethanol, ethyl citrate, water/ethanol mixtures, limonene or other terpenes, isoparaffins, glycol ethers and glycol ether esters.

A solid carrier may be, for example, absorbing gums or polymers, or yet encapsulating materials, such as wall-forming and plasticizing materials, such as mono, di- or trisaccharides, natural or modified starches, hydrocolloids, cellulose derivatives, polyvinyl acetates, polyvinylalcohols, proteins or pectins, or the like. Encapsulation is a process which is well known to a person skilled in the art, and may be performed, for example, using techniques such as spray-drying, agglomeration or yet extrusion; or consists of a coating encapsulation, including coacervation and complex coacervation techniques.

The term "perfumery base" means compositions comprising at least one perfuming co-ingredient. A "perfuming co-ingredient" can be a compound used in a perfuming preparation or composition known by one of skill in the art to impart or modify the odor of a composition. The compounds of the invention exhibit interesting fragrance properties or odor characteristics, and may be used to impart, improve, enhance or modify the odor of a wide variety of products, or it may be used as a component of a perfume (or fragrance composition) to contribute its odor character to the overall odor of such perfume. For the purposes of this invention a perfume can be a mixture of fragrance materials which is used to impart a desired odor to the skin and/or any product for which an agreeable odor is desirable.

It is contemplated that more than one perfume compound or composition can be used in the methods or articles of the present invention. The nature and type of the perfuming co-ingredients can be selected by one of skill in the art according to the intended use or application and the organoleptic effect desired. In general terms, these perfuming co-ingredients belong to chemical classes as varied as alcohols, aldehydes, ketones, esters, ethers, acetates, nitrites, terpene hydrocarbons, nitrogenous or sulphurous heterocyclic compounds and essential oils, and said perfuming co-ingredients can be of natural or synthetic origin. It is also understood that said co-ingredients may also be compounds known to release in a controlled manner various types of perfuming compounds.

Examples of perfumed articles include, but are not limited to, solid or liquid detergents, a fabric softener, an air freshener, a fabric refresher, ironing water, a paper, a wipe or a bleach The perfumed articles can be intended for domestic or industrial use. Other perfumed articles can be, for example, perfumes, colognes or after-shave lotions, perfumed soaps, shower or bath salts, mousses, oils or gels, hygiene products or hair care products, deodorants or antiperspirants, and cosmetic preparations.

The invention also includes a mixture comprising the compound of Formula (1) and an auxiliary ingredient compatible with the compound of Formula (1), the weight ratio of the compound of Formula (1) being in the range of from about 1:1 up to about 1:5. As used herein, an "auxiliary ingredient" can be, for example, thickeners, vitamins, provitamins, anti-grease agents, antioxidants, preservatives, perfumes and UV-light absorbing inorganic pigments. As used herein, "weight ratio" refers to a mixture amount.

The invention also includes a fragrance modifying composition comprising the compound of Formula (1) and an auxiliary ingredient compatible with the compound of Formula (1), the weight ratio of the compound of Formula (1) being in the range of from about 1:1 up to about 1:5.

Also included in the invention is a perfume composition comprising the compound of Formula (1) and at least one compatible adjuvant, the ratio of the compound of Formula (1) being in the range of from about 1:1 up to about 1:5. As used herein, a "compatible adjuvant" can be, for example, thickeners, vitamins, provitamins, anti-grease agents, antioxidants, preservatives, perfumes and UV-light absorbing inorganic pigments.

The invention also includes a cologne composition comprising the compound of Formula (1) and at least one compatible adjuvant, the ratio of the compound of Formula (1) being in the range of from about 1:1 up to about 1:5. Additionally, the invention includes a method of using the compound of Formula (1) as a perfume. In one embodiment, the method of using the compound of Formula (1) as a perfume further comprises an auxiliary ingredient compatible with the compound of Formula (1).

The following examples are provided for the purpose of illustrating the present invention and are not to be considered limiting.

Example 1

Production of Premnaspirodiene (2)

In this example premnaspirodiene was produced by expressing the *Hyoscyamus muticus* premnaspirodiene synthase (the "HPS") gene in *Saccharomyces cerevisiae*.

The HPS gene was cloned into the yeast shuttle expression vector YEp-GW-URA-NheI/BamHI as described in (1) to give YEp-HPS-ura. This vector contained the ADH1 promoter for initiating transcription of the HPS gene. In addition, it contained the ADH1 terminator downstream of the HPS gene. This vector was maintained in *S. cerevisiae* by selecting media lacking uracil and it was maintained in *E. coli* by selecting for resistance to ampicillin.

For production, YEp-HPS-ura was transformed into Cali-5 using the yeast transformation kit (Sigma). Transformants were selected on SDE-ura medium (0.67% Bacto yeast nitrogen base without amino acids, 2% glucose, 0.14% yeast synthetic drop-out medium supplement without uracil, 40 mg/L ergosterol). Colonies were picked and screened for premnaspirodiene production.

Cali-5 was previously engineered to overproduce farnesyl diphosphate (the "FPP"), the substrate for the HPS enzyme. It contained the following mutations: erg9, sue, dpp1. It also contained approximately 8 copies of the truncated HMG2 gene. The truncated form of HMG2 is driven by the GPD promoter and no longer under tight regulation and allows for an increase in carbon flow to FPP. Cali-5 is a derivative of SW23B, described in U.S. Pat. No. 6,689,593 to Millis et al., incorporated by this reference.

Due to the volatile nature of sesquiterpenes, it is necessary to sequester them during the fermentation process. One such sequestration method is the addition of the hydrophobic resin Amberlite XAD-16 (Sigma). This resin has been used in fermentation of other microorganisms to capture natural products as they are produced (2, 3, 4).

Production was carried out in a 14 L fermentation tank (Bioflow 110). Eight liters of fermentation medium was prepared and autoclaved in the fermentation tank (160 g $(NH_4)_2SO_4$, 160 g $KH_2PO_4$, 8 g NaCl, 48 g $MgSO_4.7H_2O$, 32 g yeast extract (Difco). Afterwards the following components were added: 160 ml mineral solution ($FeSO_4.7H_2O$ 0.028%, $ZnSO_4.7H_2O$ 0.029%, $CuSO_4.5H_2O$ 0.008%, $Na_2MoO_4.2H_2O$ 0.024%, $CoCl_2.6H_2O$ 0.024%, $MnSO_4.H_2O$ 0.017%, HCl 1 ml), 80 ml 50% glucose, 240 ml vitamin solution (biotin 0.001%, Ca-pantothenate 0.012%, inositol 0.06%, pyridoxine-HCl 0.012%, thiamine-HCl 0.012%), 80 ml 10% $CaCl_2$, and 200 g autoclaved XAD-16 beads; the beads were autoclaved in water and the water removed before adding them to the medium. Finally, 8 ml of 50 mg/ml ergosterol in 100% ethanol was added. The ergosterol was mixed with the 100% ethanol and incubated in a hot water bath to aid in the dissolving of the ergosterol. Although the ergosterol does not completely dissolve in the ethanol, the complete mixture was added to the medium.

The seed culture for inoculating the fermentation medium was prepared by inoculating 50 ml of SDE-ura medium with Cali-5 YEp-HPS-ura. This culture was grown until early stationary phase (24-48 hr). One ml of this culture was inoculated into 500 ml of SDE-ura medium and grown for 24 hr. A 400 ml aliquot (5% inoculum) was used to inoculate the 8 L of medium.

The fermentor was maintained at 28° C. The air flow was 4.5 L/min and the $pO_2$ was maintained above 20% by adjusting the rpm. Furthermore, pH was maintained at 4.5 using acetic acid and NaOH.

Once the glucose was below 1 g/L, after approximately 14 hours, a glucose feed was attached and fed at a rate of 30 ml/hr. The glucose feed was made by mixing 1400 ml 60% glucose and 328 ml 12.5% yeast extract.

After 5 days, the air and agitation were turned off, and the XAD-16 resin was allowed to settle to the bottom of the tank, for approximately 30 minutes. The broth was then siphoned off and the beads collected in a 2 L flask. The beads were washed with 2×2 L of deionized water. After removing as much of the water with a pipette as was possible, 250 ml of 100% methanol was added. The mixture was incubated at room temperature for at least an hour and then the methanol extract was removed and discarded. To elute the premnaspirodiene, 4×500 ml of methanol was used. After the addition of methanol for each extraction, the beads and methanol were warmed to 45° C. to aid in the recovery. The methanol extracts were pooled and concentrated in vacuo to 500 to 800 ml.

Because a significant amount of premnaspirodiene remained attached to the cells, the medium from the fermentation tank was allowed to sit in large glass vessels for 1 to 2 days at room temperature. This was enough time for the yeast cells to settle to the bottom of the tank. At this point, most of the medium was siphoned off. The remaining broth and cells were then collected by centrifugation.

To the cell pellet was added 250 ml of acetone. The cells were resuspended and the mixture was mixed for 10 minutes. The mixture was centrifuged for 10 minutes to pellet the cells. The acetone was removed and another 250 ml of acetone was added to the cell pellet. The solution was mixed for 10 minutes and centrifuged again. The acetone was removed and added to the first acetone extract. The acetone pools were concentrated in vacuo to approximately 250 ml.

The acetone extract was mixed with the methanol extract. This premnaspirodiene was extracted from the acetone/methanol solution with 3×300 ml of pentane. The pentane extracts were pooled and concentrated in vacuo to afford a solution of premnaspirodiene 40-50% pure. The crude material was purified on a silica gel column (100% hexane) to afford the title compound as a colorless oil (3.35 g, 91.4% pure by GC/MS). $^1$H NMR ($CDCl_3$): 0.91 (d, 3H), 1.43 (m, 1H), 1.57 (m, 4H), 1.68 (s, 3H), 1.73 (m, 6H), 1.84 (m, 2H), 2.01 (m, 1H), 2.47 (m, 1H), 4.71 (d, 2H), 5.29 (s, 1H); ESIMS m/z 205 (M+H).

Example 2

Production of Premnaspirodiene Using Vegetable Oil as Sequestering Agent

As described in Example 1, YEp-HPS-ura was transformed into strains CALI-5 or ALX7-95, a leucine prototrophic derivative of CALI-5, using the yeast transformation kit (Sigma). Transformants were selected on SDE-ura medium (0.67 Bacto yeast nitrogen base without amino acids, 2% glucose, 0.14% yeast synthetic drop-out medium without uracil, 40 mg/L ergosterol). Colonies were picked and screened for premnaspirodiene production.

Due to the volatile nature of sesquiterpenes, it is necessary to sequester them during the fermentation process. A second such sequestration method is the addition of vegetable oil to the fermentor to capture the nonpolar sesquiterepene hydrocarbon.

Production was carried out in a 14-L fermentation tank (Bioflow 110). Eight liters of fermentation medium was prepared and autoclaved in the fermentation tank (160 g $(NH_4)_2SO_4$, 160 g $KH_2PO_4$, 8 g NaCl, $MgSO_4.7H_2O$, 32 g yeast extract (Difco). Afterward the following components were added: 160 ml mineral solution (0.028% $FeSO_4.7H_2O$. 0.029% $ZnSO_4.7H_2O$, 0.008% $CuSO_4.5H_2O$, 0.024% $Na_2MoO_4.2H_2O$, 0.024% $CoCl_2.6H_2O$, 0.017% $MnSO_4.H_2O$, 1 mL HCl); 80 mL 50% glucose; 240 mL vitamin solution (0.001% biotin; 0.012% calcium pantothenate, 0.06% inositol, 0.012% pyridoxine-HCl, 0.012% thiamine-HCl); 80 mL 10% $CaCl_2$, and 200 mL autoclaved soybean oil (purchased from local groceries). Finally, 8 mL of 50 mg/mL cholesterol in 100% ethanol was added.

The seed culture for inoculating the fermentation medium was prepared by inoculating 50 mL of SDE-ura medium with CALI-5 or ALX7-95 containing YEp-HPS-ura. This culture was grown until early stationary phase (24-48 hr). One mL of this culture was inoculated into 500 mL of SDE-ura medium and grown for 24 hr. A 400-mL aliquot (5% inoculum) was used to inoculate the 8 L of medium.

The fermentor was maintained at 26° C. The air flow was 4.5 L/min and the $dO_2$ was maintained above 30% by adjusting the rpm. Furthermore, the pH was maintained at 4.5 using acetic acid and NaOH.

Once the glucose concentration was below 1 g/L, a feeding regimen was initiated such that the glucose in the fermentor was kept between 0 and 1 g/L. The glucose feed was made by mixing 1400 mL of 60% glucose and 328 mL of 12.5% yeast extract.

After 5 days, the air and agitation were turned off, and the oil was allowed to rise to the top of the tank and decanted.

Example 3

Preparation of 2-Isopropenyl-6,10-dimethyl-spiro [4.5]dec-6-en-8-one (the "(−)-solavetivone") (5)

3,5-Dimethylpyrazole (47 g, 0.49 mol) was dissolved in a mixture of $CH_2Cl_2$ (650 mL) and t-butyl alcohol (31 mL). The solution was then cooled to −78° C. Chromyl chloride ($CrO_2Cl_2$) (13.3 mL) was added over 15 min and stirred for another 15 min before it was allowed to warm to room temperature. Premnaspirodiene (6.69 g, 32.7 mmol) was dissolved in $CH_2Cl_2$ (650 mL) and added rapidly to the reaction. The dark red solution was stirred for 48 hours. The reaction was concentrated under vacuum and the residue was suspended in ether. The suspension was then filtered through Celite to remove most of the chromium. The supernatant was then diluted to a 1:1 mixture with hexane. The suspension was filtered through a pad of silica to remove some of the 3,5-dimethylpyrazole. After evaporation under vacuum, the residue was purified on a silica gel column (hexane:ether, 9:1, hexane:ether, 2:1) to afford the title compound as a light yellow oil (3.45 g, 48.3%). $^1$H NMR (CDCl$_3$): 1.00 (d, 3H), 1.59 (m, 2H), 1.68 (m, 1H), 1.76 (s, 3H), 1.93 (m, 5H), 2.11 (m, 2H), 2.21 (dd, 1H), 2.55 (m, 1H), 2.66 (dd, 1H), 4.74 (dd, 2H), 5.75 (s, 1H); ESIMS m/z 219 (M+H).

Example 4

Preparation of 2-Isopropylidene-6,10-dimethyl-spiro [4.5]dec-6-en-8-one (the "5-epi-β-vetivone") (1)

To a solution of (−)-solavetivone (5) (1.66 g, 7.62 mmol) dissolved in ethanol (16 mL) was added Amberlyst® IR-15 (1.66 g). The suspension was then heated at 100° C. in a sealed reaction flask for 50 min. The suspension was then filtered through Celite and evaporated under vacuum. The residue was purified on a silica gel column (hexane:ether, 85:15). Fractions were analyzed by GC/MS and only fractions with a purity of >95% were retained. Fractions with purities of 50-94% were combined and repurified. This process was repeated until 3 silica gel columns have been run. Final consolidation of all three purifications yielded the title compound as a colorless oil (700 mg, 42.2%). $^1$H NMR (CDCl$_3$): 0.93 (d, 3H), 1.58 (s, 6H), 1.82 (m, 3H), 1.86 (s, 3H), 2.05 (m, 1H), 2.16 (dd, 1H), 2.37 (m, 3H), 2.57 (dd, 1H), 5.75 (s, 1H); ESIMS m/z 219 (M+H).

Example 5

Preparation of 2-Isopropyl-6,10-dimethyl-spiro[4.5] deca-2,6-dien-8-one (3) & 2-Isopropyl-6,10-dimethyl-spiro[4.5]deca-1,6-dien-8-one (4)

To a solution of (−)-solavetivone (5) (100 mg, 0.46 mmol) dissolved in ethanol (2 mL) was added Amberlyst® IR-15 (150 mg). The suspension was then heated at 105° C. in a sealed reaction flask for 96 hours. The suspension was then filtered through Celite and evaporated under vacuum. The residue was purified on a silica gel column (hexane:ether, 85:15) to afford the mixture as a colorless oil (67 mg, 67%). ESIMS m/z 219 (M+H), 78.7% at 14.71 min; 219 (M+H), 17.1% at 14.89 min.

Example 6

Oxidation of (+)-Valencene to (+)-Nootkatone

In order to test various reaction conditions for the oxidation of premnaspirodiene to solavetivone, reactions were carried out on commercially available valencene, a compound that is chemically similar to premnaspirodiene and would be expected to oxidized under similar reaction conditions. Reactions were carried out using 250 mg of starting material in a single reaction, using combinations of sodium chlorite and either t-butylhydroperoxide (t-BuOOH) or N-hydroxyphthalimide (NHPI) as described (S. M. Silvestre & J. A. R. Salvador, "Allylic and Benzylic Oxidation Reactions with Sodium Chlorite," *Tetrahedron* 63: 2439-2445 (2007)). The conditions used were those shown in Table 1. Of the conditions tested, that used in Experiment 1a (Table 1) gave the highest yield and the fewest byproducts. In Experiment 1a, the only byproduct observed was unreacted starting material.

TABLE 1

Oxidation of (+)-Valencene to (+)-Nootkatone

| Exp | NaClO$_2$ (equiv) | t-BuOOH (equiv) | NHPI (equiv) | % Product hplc | # of byproducts |
|-----|-------------------|-----------------|--------------|----------------|-----------------|
| 1a  | 1.2               | 5.0             | NA           | 75%            | 1               |
| 1b  | 1.2               | 3.0             | NA           | 65%            | 1               |
| 1c  | 2.1               | 5.0             | NA           | 45%            | 2               |
| 1d  | 2.5               | 5.0             | NA           | 45%            | 2               |
| 2a  | 1.5               | NA              | 0.1          | 60%            | 3               |
| 2b  | 1.5               | NA              | 0.5.         | 65%            | 3               |
| 2c  | 2.0               | NA              | 0.1          | 40%            | 3               |
| 2d  | 3.0               | NA              | 0.1          | 25%            | 3               |

In a first oxidation procedure on a larger quantity of (+)-valencene carried out according to Experiment 1a of Table 1, (+)-valencene (1.0 g, 4.9 mmol, 1.0 equiv.) was placed in a four-neck 250-mL flask equipped with a nitrogen inlet tube, thermowell, and a mechanical stirrer. Acetonitrile (45 mL) and water (15 mL) were added to the flask. A 70% solution in water of t-butyl hydroperoxide (3.15 g, 24.5 mmol, 5 equiv.) was added to the solution followed by the slow addition of sodium chlorite (80%) (0.66 g, 5.9 mmol, 1.2 equiv.). The reaction was heated to 50° C. for 18 h; it was then cooled and poured info a 10% solution of sodium sulfite (100 mL). This solution was then extracted with diethyl ether (100 mL). The organic layer was washed with saturated sodium bicarbonate (50 mL), dried over sodium sulfate and absorbed onto silica gel (2 g). This material was then purified on a silica gel column (20 g) and eluted with 5% ethyl acetate in heptane (250 mL) and 10% ethyl acetate in heptane (250 mL). The fractions containing the desired product were combined and concentrated under reduced pressure to give the desired product in 72% yield (0.48 g).

In a second oxidation procedure on a larger quantity of (+)-valencene carried out substantially according to Experiment 2a of Table 1, except that the quantity of sodium chlorite was reduced from 1.5 equivalents to 1.2 equivalents, (+)-valencene (1.0 g, 4.9 mmol, 1.0 equiv.) was placed in a four-neck 250-mL flask equipped with a nitrogen inlet tube, thermowell, and a mechanical stirrer. Acetonitrile (45 mL) and water (15 mL) were added to the flask. N-hydroxyphthalimide (80 mg, 0.05 mmol, 0.1 equiv.) was added to the solution followed by the slow addition of sodium chlorite (80%) (0.66 g, 5.9 mmol, 1.2 equiv.) The reaction was heated to 50° C. for 18 h; it was then cooled and poured into a 10% solution of sodium sulfite (100 mL). This solution was then extracted with diethyl ether (100 mL). The organic layer was washed with saturated sodium bicarbonate (50 mL), dried over sodium sulfate, and absorbed onto silica gel (2 g). This material was then purified on a silica gel column (20 g) and eluted with 5% ethyl acetate in heptane (250 mL) and 10% ethyl acetate in heptane (250 mL). The fractions containing the desired product were combined and concentrated under reduced pressure to give the desired product in 52% yield (0.37%).

Example 7

Oxidation of Premnaspirodiene to 5-Epi-β-Vetivone

To verify these conditions for premnaspirodiene, a larger scale reaction was carried out as follows: (−)-Premnaspirodiene (distilled from vegetable oil, ~90% purity) (1.0 g, 4.6 mmol, 1.0 equiv.) was placed in a four-neck 250 mL flask equipped with a nitrogen inlet tube, thermowell, and a mechanical stirrer. Acetonitrile (45 mL) and water (15 mL)

were added to the flask. A 70% solution in water of t-butyl hydroperoxide (2.94 g, 23 mmol, 5 equiv.) was added to the solution followed by the slow addition of sodium chlorite (80%) (0.63 g, 5.5 mmol, 1.2 equiv.). The reaction was heated to 50° C. for 18 h. Very little conversion of starting material was seen at this point, as determined by gas chromatography, likely due to the poor solubility in acetonitrile/water. t-Butanol was added (15 mL) and the homogenous reaction was heated for an additional 16 h at 50° C. The reaction was then cooled and poured into a 10% solution of sodium sulfite (100 mL). The solution was then extracted with diethyl ether (100 mL). The organic layer was washed with saturated sodium bicarbonate (50 mL), dried over sodium sulfate, and adsorbed onto silica gel. The material was purified on a silica gel column (20 g) and eluted with 5% ethyl acetate in heptane (250 mL) and 10% ethyl acetate in heptane (250 mL). Fractions containing (−)-solavetivone, as determined by gas chromatography and confirmed by nuclear magnetic resonance (NMR), were combined and concentrated to give the desired product. The yield was 18%.

Example 8

Distillation of Premnaspirodiene

As described above, engineered yeast strains expressing the *Hyoscyamus muticus* premnaspirodiene synthase gene were grown in fermentors containing vegetable oil (soybean oil purchased from local groceries). The oil layers were collected and pooled from numerous fermentations and subjected to distillation under the conditions described below.

Distillation was carried out in a Pope still (wiped-film) at 100° C. and a pressure of 350 mTorr. Recovery was 4.05 g (3.96% of a ~4% solution). Analysis by gas chromatography of the oil prior to distillation and of the purified premnaspirodiene distilled from the oil indicated that the distilled product was very similar to the product contained in the oil. Recovery was virtually 100% as indicated by a lack of the detectable premnaspirodiene in the vegetable oil following distillation. The purity of the distilled premnaspirodiene was estimated to be 92%.

Figure 7:
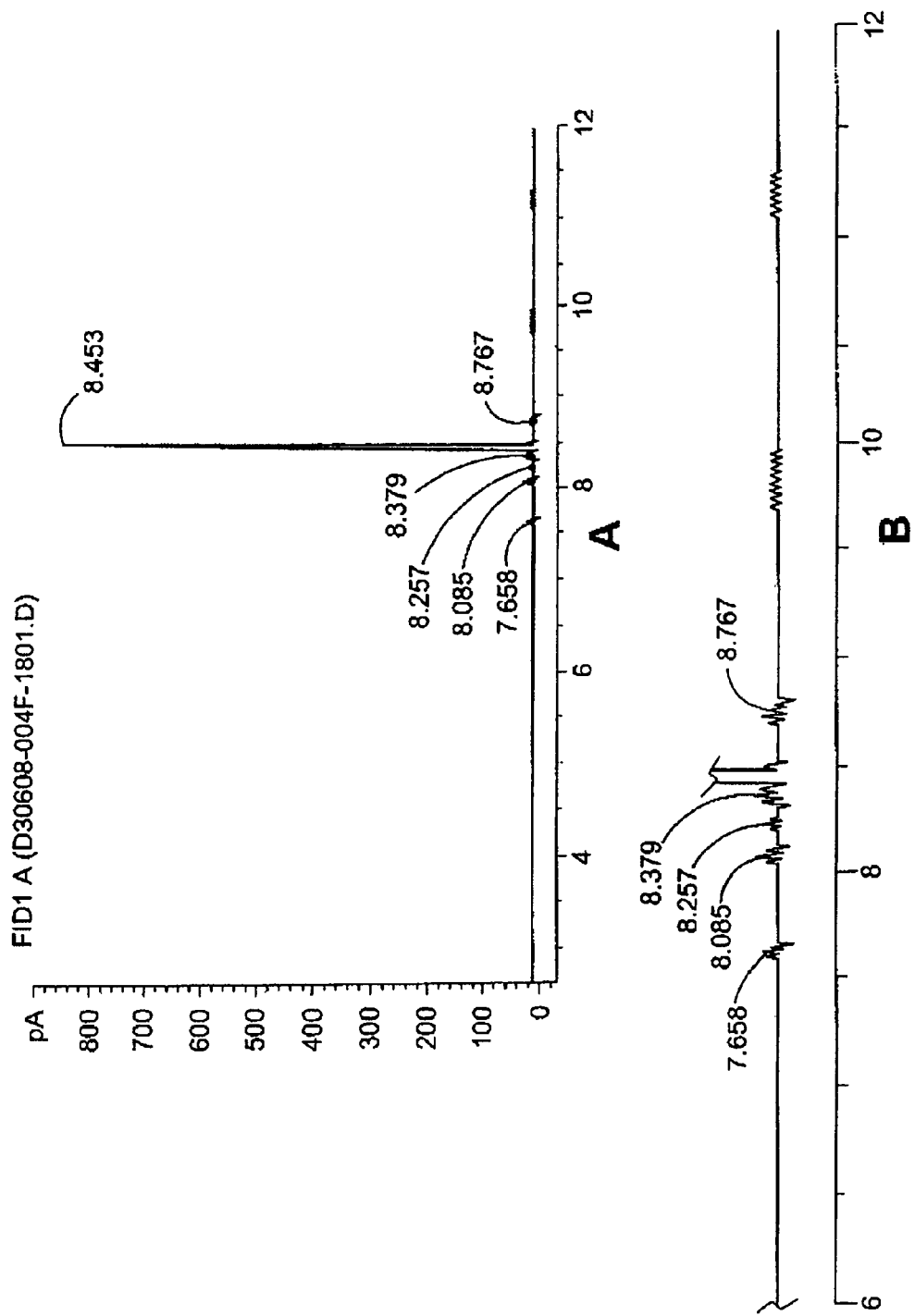
FIG. 7 provides a graph showing the GC trace of premnaspirodiene in vegetable oil before distillation (Example 8).
Figure 8:
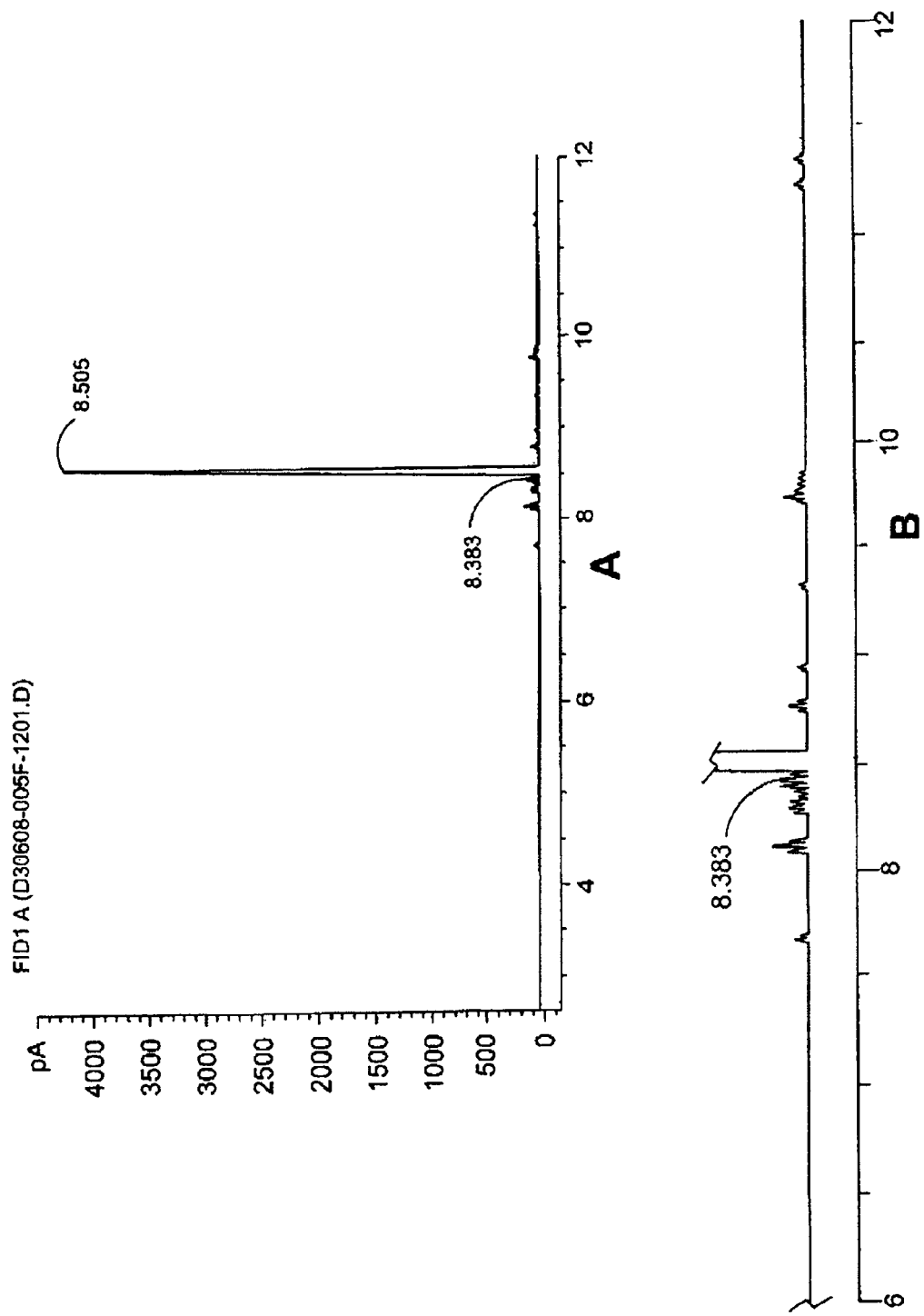
FIG. 8 provides a graph showing the GC trace of purified premnaspirodiene after distillation (Example 8).

The gas chromatography (GC) trace of premnaspirodiene in vegetable oil before distillation is shown in FIG. 7. FIG. 7A shows the graph on normal scale. FIG. 7B expands the scale to depict the impurities present in the premnaspirodiene before distillation. FIG. 8 provides a graph showing the GC trace of purified premnaspirodiene after distillation. FIG. 8A shows the graph on a normal scale. FIG. 8B expands the scale to depict the lack of impurities present in the premnaspirodiene after distillation.

Example 9

Evaluation of 5-epi-β-vetivone

The intensity and longevity of a fragrance is based on the concentration, intensity and longevity of the aromatic compounds used.

The performance of 5-epi-β-vetivone (EBV) as a fragrance was evaluated. EBV was compared to Nootkatone (CAS: 4674-50-4) daily over a period of thirty days. The evaluation mixture contained a 10% solution of each molecule in Isopropyl Myristate (CAS: 110-27-0). The evaluation was performed by three trained perfumers.

The results of the evaluation are listed in Table 2. Each compound was rated on a scale of 1 (no detectable odor) to 10 (strength of the 10% Nootkatone solution on Day 1). The initial strength of EBV was perceived as roughly "half as intense" as Nootkatone. While EBV was noticeably weaker then Nootkatone, it was still detectable after approximately three weeks. However, each compound diminished in strength after three weeks, and both compounds exhibited similar degradation. EBV remained proportionally weaker than Nootkatone.

TABLE 2

|  | Nootkatone Pure (>98%) Strength | 5-epi-β-vetivone (95.1%) Strength |
| --- | --- | --- |
| Day 0 | 10 | 6 |
| Day 7 | 9 | 5 |
| Day 14 | 7 | 3 |
| Day 21 | 5 | 2 |
| Day 28 | 4 | 2 |

A fragrance can be classified or described according to the elements of its character. The characters of both EBV and Nootkatone was described as grapefruit, woody, and vetivert. Close and repeated evaluation of the two compounds indicated that EBV is similar, but slightly more "woody" in character than Nootkatone, which is more "grapefruit" in character. As such, EBV has a better, more desirable smell then currently available compounds. Perfumers found the character of both compounds to change relatively little over a three week period. Additionally, EBV was found to be moderately stable. The results indicate that EBV has a long-lasting, woody, vetiver note that is not bound by natural or botanical supply constraints and introduces little or no potential for color problem.

REFERENCES

The following references are cited in the specification and examples by reference number; all of these references are incorporated by this reference in the application in their entirety.

1) Hwu, J. R.; Wetzel, J. M., *J. Org. Chem.* (1992), 57(3), 922-928.
2) Endo, K.; de Mayo, P., *Chem. Pharm. Bull* (1969), 17, 1324.
3) Hunter, G. L. K.; Brogden, W. B., Jr., *J. Food Sci.* (1965), 30, 876.
4) Wilson III, C. W.; Shaw, P. E., *J. Agric. Food Chem.* (1978), 26(6), 1430-1432.
5) Salvador, J. A. R.; Melo, M. L.; Campos Neves, A. S., *Tetrahedron Letters* (1997), 38(1), 119-122.
6) Arantes, S. F.; Farooq, A.; Hanson, J. R., *Journal of Chemical Research*, (1999), (3), 248.
7) Salvador, J. A. R.; Clark, J. H., *Green Chemistry*, (2002), 4(4), 352-356.
8) Butterworth, A. J.; Clark, J. H.; Walton, P. H.; Barlow, S. J., *Chemical Communications*, (1996), (16), 1859-1860.
9) Chisem, J.; Chisem, T. C.; Rafelt, J. S. Macquarrie, D. J.; Clark, J. H., *Chemical Communications*, (1997), (22), 2203-2204.
10) Van Der Gen, A.; Van Der Linde, L. M.; Witteveen, J. G.; Boelens, H., *Recueil des travaux chimiques des Pays-Bas* (1971), 90, 1045-1054.
11) Takemoto, Y.; Kuraoka, S.; Ohra, T.; Yonetoku, Y.; Twata, C., *Tetrahedron* (1997), 53(2), 603-616.

12) Takahashi, S., Yeo, Y., Greenhagen, B. T., McMullin, T., Song, L., Maurina-Brunker, J., Rosson, R., Noel, J. P., Chappell, J. (2006) Metabolic engineering of sesquiterpene metabolism in yeast. Biotechnology and Bioengineering. In Press. (Published on-line Sep. 29, 2006).
13) Woo E J, Starks C M, Carney J R, Arslanian R, Cadapan L, Zavala S, Licari P (2002) Migrastatin and a new compound, isomigrastatin, from *Streptomyces platensis*. J Antibiot 55:141-146.
14) Julien B, Shah S (2002) Heterologous expression of the epothilone biosynthetic genes in *Myxococcus xanthus*. Antimicrob Agents Chemother 46:2772-2778.
15) Frykman, S., Tsuruta, H., Galazzo, J., Licari, P. (2006) Characterization of product capture resin during microbial cultivations. J Ind Microbiol Biotechnol. 33:445-453.

ADVANTAGES OF THE INVENTION

The present invention provides novel and efficient methods for the production and isolation of 5-epi-β-vetivone, 2-isopropyl-6,10-dimethyl-spiro[4.5]deca-2,6-dien-8-one and 2-isopropyl-6,10-dimethyl-spiro[4.5]deca-1,6-dien-8-one, which are useful for their fragrant properties. These methods use premnaspirodiene as a starting material, and the present invention also provides novel and efficient methods for the production of premnaspirodiene from a readily-available terpene substrate.

The present invention provides highly purified 5-epi-β-vetivone, 2-isopropyl-6,10-dimethyl-spiro[4.5]deca-2,6-dien-8-one and 2-isopropyl-6,10-dimethyl-spiro[4.5]deca-1,6-dien-8-one in high yield, requiring a limited number of reaction steps and using inexpensive and readily available starting materials.

The present invention possesses industrial applicability because the products, namely 5-epi-β-vetivone, 2-isopropyl-6,10-dimethyl-spiro[4.5]deca-2,6-dien-8-one and 2-isopropyl-6,10-dimethyl-spiro[4.5]deca-1,6-dien-8-one, are capable of industrial use and application as fragrances and for other purposes.

With respect to ranges of values, the invention encompasses each intervening value between the upper and lower limits of the range to at least a tenth of the lower limit's unit, unless the context clearly indicates otherwise. Moreover, the invention encompasses any other stated intervening values and ranges including either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test this invention.

The publications and patents discussed herein are provided solely for their disclosure prior to the filing date of the present application. Nothing herein is to be construed as an admission that the present invention is not entitled to antedate such publication by virtue of prior invention. Further the dates of publication provided may be different from the actual publication dates which may need to be independently confirmed.

All the publications cited are incorporated herein by reference in their entireties, including all published patents, patent applications, literature references, as well as those publications that have been incorporated in those published documents. However, to the extent that any publication incorporated herein by reference refers to information to be published, applicants do not admit that any such information published after the filing date of this application to be prior art. Similarly, all GenBank sequences and other sequence information obtainable from publicly accessible databases are herein incorporated by reference as if each was specifically and individually indicated to be incorporated by reference.

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of a Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

We claim:
1. A method for producing (−)-premnaspirodiene from a terpene substrate, comprising the steps of:
(a) providing a terpene substrate to a host cell transformed or transfected with a vector comprising a sequence of nucleic acid residues encoding a premnaspirodiene synthase gene;
(b) culturing the host cell by fermentation under conditions suitable to produce (−)-premnaspirodiene from the terpene substrate, wherein:
the fermentation system comprises an aqueous and a nonpolar solvent phase;

the non-polar solvent phase is substantially immiscible with the aqueous phase; and the premnaspirodiene is sequestered in the non-polar solvent phase during fermentation; and (c) isolating the (−)-premnaspirodiene from the non-polar solvent phase.

2. The method of claim 1, wherein the step of providing the terpene substrate is performed by synthesis of the terpene substrate by the host cell.

3. The method of claim 2, wherein the terpene substrate is farnesyl diphosphate.

4. The method of claim 1, wherein the host cell is a eukaryotic cell.

5. The method of claim 4, wherein the host cell is a yeast cell.

6. The method of claim 5, wherein the host cell is a *Saccharomyces cerevisiae* cell.

7. A method for producing (−)-premnaspirodiene from a terpene substrate, comprising the steps of:

(a) providing a terpene substrate to a host cell transformed or transfected with a vector comprising a sequence encoding a premnaspirodiene synthase gene;

(b) culturing the host cell under conditions suitable to produce (−)-premnaspirodiene from the terpene substrate, wherein the (−)-premnaspirodiene is sequestered as it is produced during the culturing step; and (c) isolating the (−)-premnaspirodiene.

8. The method of claim 1, wherein the (−)-premnaspirodiene is isolated from the non-polar solvent phase by distillation.

9. The method of claim 8, wherein the non-polar solvent phase is a vegetable oil.

10. The method of claim 9, wherein the vegetable oil is a soybean oil.

11. The method of claim 8, wherein the non-polar solvent phase is a high-molecular weight aliphatic hydrocarbon selected from among a straight-chain or branched-chain isomer of dodecane, tridecane, tetradecane, pentadecane, and hexadecane, wherein the high-molecular weight aliphatic hydrocarbon optionally is substituted with one or more hydroxy or halogen substituents such that the substituted hydrocarbon is substantially immiscible with the aqueous phase.

12. The method of claim 1, wherein the premnaspirodiene synthase gene is from *Hyoscyamus muticus*.

13. The method of claim 5, wherein the yeast cell overproduces farnesyl diphosphate.

14. The method of claim 1, wherein the host cell is a bacteria, cyanobacteria, filamentous fungi or algae.

15. The method of claim 1, wherein the culturing of the host cell is performed by batch fermentation, fed-batch fermentation or continuous fermentation.

16. The method of claim 7, wherein sequestration is effected by binding the (−)-premnaspirodiene to a hydrophobic resin, and the (−)-premnaspirodiene is isolated from the resin.

17. The method of claim 7, wherein culturing is effected by fermentation.

* * * * *